(12) United States Patent
Prakash

(10) Patent No.: US 9,132,426 B2
(45) Date of Patent: Sep. 15, 2015

(54) SIMPLIFIED GATING METHOD FOR SEALING AND FLOW CONTROL IN MICRO AND NANO DEVICES

(71) Applicant: NanoMDx, Inc., Northborough, MA (US)

(72) Inventor: Ranjit A. Prakash, Northborough, MA (US)

(73) Assignee: NanoMDx, Inc., Northborough, MA (US)

( * ) Notice: Subject to any disclaimer, the term of this patent is extended or adjusted under 35 U.S.C. 154(b) by 0 days.

(21) Appl. No.: 14/303,084

(22) Filed: Jun. 12, 2014

(65) Prior Publication Data

US 2014/0328733 A1 Nov. 6, 2014

Related U.S. Application Data

(62) Division of application No. 13/955,690, filed on Jul. 31, 2013.

(60) Provisional application No. 61/678,364, filed on Aug. 1, 2012.

(51) Int. Cl.
*G01N 15/06* (2006.01)
*G01N 33/00* (2006.01)
(Continued)

(52) U.S. Cl.
CPC ........... *B01L 3/567* (2013.01); *B01L 3/502715* (2013.01); *B01L 3/502738* (2013.01); *C12Q 1/6837* (2013.01); *B01L 3/502723* (2013.01); *B01L 2200/027* (2013.01); *B01L 2200/0605* (2013.01); *B01L 2200/16* (2013.01); *B01L 2300/0816* (2013.01); *B01L 2300/0867* (2013.01); *B01L 2300/0883* (2013.01); *B01L 2400/0487* (2013.01); *B01L 2400/06* (2013.01);

(Continued)

(58) Field of Classification Search
USPC .................. 422/50, 68.1, 502, 503, 504, 537; 436/43, 180
See application file for complete search history.

(56) References Cited

U.S. PATENT DOCUMENTS 6,238,868 B1 5/2001 Carrino et al.
6,576,459 B2 6/2003 Miles et al.
(Continued)

FOREIGN PATENT DOCUMENTS

KR 20090041973 4/2009
WO WO-02/43864 A2 6/2002
(Continued)

OTHER PUBLICATIONS

International Search Report and Written Opinion for International Patent Application No. PCT/US2013/053284 mailed Feb. 14, 2014. 14 pages.

*Primary Examiner* — Brian J Sines
(74) *Attorney, Agent, or Firm* — Wilmer Cutler Pickering Hale and Dorr LLP

(57) ABSTRACT

A biochip for multiplex genetic identification is disclosed. An biochip for separating and detecting a plurality of DNA fragments includes a set of inputs and chambers for receiving a sample matrix of genetic material and reagents needed to conduct a polymerase chain reaction amplification of the genetic material. The biochip also includes a plurality of separation and detection chambers that physically separate different DNA fragments that have been marked with labels that emit similar colors, thereby enabling the independent detection of the different DNA fragments.

8 Claims, 19 Drawing Sheets

(51) Int. Cl.
*G01N 33/48* (2006.01)
*B01L 3/00* (2006.01)
*C12Q 1/68* (2006.01)

(52) U.S. Cl.
CPC .. *B01L 2400/0638* (2013.01); *B01L 2400/0655* (2013.01)

(56) References Cited

U.S. PATENT DOCUMENTS

| | | | |
|---|---|---|---|
| 6,664,104 B2 | 12/2003 | Pourahmadi et al. | |
| 7,142,738 B2 | 11/2006 | Lee | |
| 7,172,897 B2 | 2/2007 | Blackburn et al. | |
| 7,267,948 B2 | 9/2007 | Vo-Dinh | |
| 7,338,637 B2 | 3/2008 | Pease et al. | |
| 7,524,464 B2 | 4/2009 | Ahn et al. | |
| 7,642,053 B2 | 1/2010 | Gumbrecht et al. | |
| 7,799,521 B2 * | 9/2010 | Chen | 435/6.16 |
| 7,807,454 B2 | 10/2010 | Oh et al. | |
| 7,863,035 B2 | 1/2011 | Clemens et al. | |
| 7,914,994 B2 | 3/2011 | Petersen et al. | |
| 7,932,098 B2 | 4/2011 | Childers et al. | |
| 8,021,873 B2 | 9/2011 | Johnson et al. | |
| 8,088,576 B2 | 1/2012 | Gumbrecht et al. | |
| 8,148,116 B2 | 4/2012 | Chen | |
| RE43,365 E | 5/2012 | Anderson et al. | |
| 8,202,492 B2 | 6/2012 | Linder et al. | |
| 2004/0109793 A1 | 6/2004 | McNeely et al. | |
| 2005/0074784 A1 | 4/2005 | Vo-Dinh | |
| 2005/0196760 A1 | 9/2005 | Pemov et al. | |
| 2006/0275789 A1 | 12/2006 | Willis et al. | |
| 2007/0116607 A1 | 5/2007 | Wang et al. | |
| 2008/0185057 A1 * | 8/2008 | Prakash et al. | 137/594 |
| 2009/0023603 A1 | 1/2009 | Selden et al. | |
| 2009/0148933 A1 | 6/2009 | Battrell et al. | |
| 2010/0021910 A1 | 1/2010 | Cao et al. | |
| 2010/0055771 A1 | 3/2010 | Yoo | |
| 2010/0144558 A1 | 6/2010 | Zenhausern et al. | |
| 2010/0184020 A1 | 7/2010 | Beer | |
| 2010/0186524 A1 | 7/2010 | Ariessohn et al. | |
| 2010/0274155 A1 | 10/2010 | Battrell et al. | |
| 2010/0311070 A1 | 12/2010 | Oh et al. | |
| 2011/0086352 A1 | 4/2011 | Bashir et al. | |
| 2011/0111987 A1 | 5/2011 | Siegrist et al. | |
| 2011/0136262 A1 | 6/2011 | Ragavan et al. | |
| 2011/0180425 A1 | 7/2011 | Kayyem | |
| 2011/0244467 A1 | 10/2011 | Haswell | |
| 2011/0312518 A1 | 12/2011 | Davis et al. | |
| 2011/0312646 A1 | 12/2011 | Silverbrook et al. | |
| 2011/0312755 A1 | 12/2011 | Silverbrook et al. | |
| 2012/0003659 A1 | 1/2012 | Yoo | |
| 2012/0052562 A1 | 3/2012 | Silverbrook et al. | |
| 2012/0070833 A1 | 3/2012 | Wang et al. | |
| 2012/0082985 A1 | 4/2012 | Zenhausern et al. | |
| 2012/0149021 A1 | 6/2012 | Yung et al. | |
| 2013/0251604 A1 * | 9/2013 | Kim et al. | 422/504 |

FOREIGN PATENT DOCUMENTS

| | | |
|---|---|---|
| WO | WO-2005/107938 A2 | 11/2005 |
| WO | WO-2006/118420 A1 | 11/2006 |
| WO | WO-2008/082712 A2 | 7/2008 |
| WO | WO-2008/124116 A1 | 10/2008 |
| WO | WO-2011156838 A1 | 12/2011 |

* cited by examiner

| ORGANISMS | FORWARD PRIMER | REVERSE PRIMER | PROBE |
|---|---|---|---|
| INFLUENZA-A/H3 | 5'-GGGCCTGTCCCAGATATGTT-3' | 5'-ATGCCTGAAACCGTACCAAC-3' | /5Cy5/ACTGACTAACAATACAAAATGGTTGGACGGAATGG-3' |
| INFLUENZA-A/H1 | 5'-TATTCCCAAGCCAAGTTCA-3' | 5'-CAGCACGAGAGACTTCTTTCC-3' | /5Cy5/ACTGACTAACAATCGAACATGAACAAGGTGTAACGGCAGCATG-3' |
| INFLUENZA-B | 5'-CGGCGAAAGCTTCAAATACTC-3' | 5'-TCTGTAGGGTCCTCCTGGTG-3' | /5Cy5/ACTGACTAACAGACTGTTACATCCGGGTGCTTCCT-3' |
| INFLUENZA-A | 5'-GCGGACAGAGACTGGAAAGTGT-3' | 5'-GCAGTCCCTGCGTCACTGG-3' | /5Cy5/ACTGACTAACATTGAGGCTTCTCATGGAATGGCTAAAGA-3' |

FIG. 19A

| COMMON QUENCHER SEQUENCE |
|---|
| 5'-TGTTATTCAGT/3IAbRQSp/ |
| 5'-TGTTATTCAGT/3IABkFQ/ |

FIG. 19B

SEQUENCE LISTING

<160> NUMBER OF SEQ ID NOS: 15

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgttattcag t                                                          11

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggcctgtcc cagatatgtt                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcctgaaa ccgtaccaac                                                 20

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 5Cy5

<400> SEQUENCE: 4
actgactaac aatagaaaat ggttgggagg gaatgg                               36

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tattccccaa gccaagttca                                                 20

<210> SEQ ID NO 6

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagcacgagg acttctttcc                                                 20

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 5Cy5

<400> SEQUENCE: 7
actgactaac atcgaacaaa ggtgtaacgg cagcatg                              37

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggcgaaagc ttcaatactc                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctgtagggt cctcctggtg                                                 20

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 5Cy5

<400> SEQUENCE: 10
actgactaac agacctgtta catccgggtg ctttcct                              37

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcagagac tggaaagtgt                                                 20
```

```
<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagtcctcg ctcactgg                                                     18

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 5Cy5

<400> SEQUENCE: 13
actgactaac attgaggctc tcatggaatg gctaaaga                                38

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' 3IAbRQSp

<400> SEQUENCE: 14
tgttattcag t                                                            11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' 3IABkFQ

<400> SEQUENCE: 15
tgttattcag t                                                            11
```

SIMPLIFIED GATING METHOD FOR SEALING AND FLOW CONTROL IN MICRO AND NANO DEVICES

CROSS-REFERENCE TO RELATED APPLICATIONS

This application is a divisional application of U.S. patent application Ser. No. 13/955,690, entitled "Functionally Integrated Device for Multiplex Genetic Identification," filed Jul. 31, 2013, which claims priority to U.S. Provisional Application No. 61/678,364, entitled "Functionally Integrated Device for Multiplex Genetic Identification," filed Aug. 1, 2012, the contents of each of which are incorporated by reference herein.

This application is related to U.S. application Ser. No. 13/955,641, entitled "Method for Separation and Detection of DNA Fragments", filed Jul. 31, 2013, and U.S. application Ser. No. 13/955,659, entitled "Enhanced Method for Probe Based Detection of Nucleic Acids", filed Jul. 31, 2013, each of which are incorporated by reference herein.

SEQUENCE LISTING

The instant application contains a Sequence Listing which has been submitted in ASCII format via EFS-Web in the parent application listed above and is hereby incorporated by reference in its entirety.

BACKGROUND OF THE INVENTION

1. Field of Invention

The invention generally relates to methods and systems for multiplex DNA analysis in an integrated biochip, and, more specifically, to methods and systems that enable multiple target DNA fragments in a sample to be detected while reducing interference between the detected targets.

2. Description of Related Art

Integrated biochips, also referred to as microfluidics or lab-on-a-chip, have gained increasing attention in recent years especially in clinical diagnostics since they are amiable for self-contained, portable, point of care devices. These devices enable performing several biotechnology tasks in a single device thereby minimizing the need for a large laboratory setup and skilled laboratory personal to perform diagnostic and research tests. Some of the popular applications of biochips include cancer detection, environmental testing, forensics, pathogen identification, gene-expression, SNP detection, to name a few.

To date there have been several demonstration of integrated biochips, some of which illustrate processing sample for cell lysis, DNA extraction, PCR (polymerase chain reaction) or isothermal amplification and detection. We use the genetic term "amplification" to mean PCR and isothermal amplifications. These terms are interchangeable unless specified otherwise. For example, the integration of sample preparation and amplification to detection strategies such as capillary electrophoresis, mass spectroscopy, qPCR, and microarray have been widely demonstrated. However, it is known that the final DNA fragment detection method determines the limitations on the number and size of the DNA fragments that can be amplified by PCR or isothermal amplification.

Typically, one amplified DNA fragment can correspond to one organism/disease identification. Hence, the ability to amplify several DNA fragments and uniquely detect each of these fragments provides a better platform for identification from a single experiment, both for research and clinical diagnostics. In this regard, in recent years multiplex PCR and isothermal amplification reactions have gained attention since it is capable of generating several DNA fragments to identify many organisms/diseases from a single reaction. Nevertheless, it is the DNA detection strategy employed post multiplex amplification that determines the number (or size) of the DNA fragments that can be uniquely detected.

Capillary electrophoresis (CE) and mass spectroscopy are popular approaches for detecting several DNA fragments generated by multiplex PCR/isothermal amplification. However, both these methods impose the limitation that the amplified DNA fragments must be of unique sizes and the sizes of the DNA fragments should be larger than the separation resolution of the instrument/system. Furthermore, both capillary electrophoresis and mass spectroscopy suffer from an inability to discriminate non-specific amplification if those non-specific DNA fragments are similar in size to any of the other DNA fragments generated by multiplex PCR/isothermal amplification. Also, since capillary or microfluidic electrophoresis in biochips utilize micro fluidic path for DNA migration, they require expensive excitation and emission optics (e.g., lasers, CCD, photomultipliers) to sensitively detect low concentration fluorescence in biochips. Nevertheless, the proven approach of CE for DNA fragment analysis has rendered this method for the widespread use in integrated biochips for over a decade.

In contrast, traditional qPCR using the TaqMan probe method has better specificity but is limited to the detection of DNA fragments that can be labeled by uniquely colored fluorophore, determined by the instrument color detection capability (e.g., known systems are believed to be limited to nine colors). Hence, integrated biochips that utilize the qPCR method are limited to scanning and identifying fewer than nine DNA fragments, if the capability of a nine color qPCR system is employed. However, qPCR systems typically only demand low cost excitation and emission optics (e.g. LED, flash lamps, and photodiodes) and this enables low-cost instrumentation for this method.

Another approach that increases detection capability for multiplex PCR/isothermal amplification is the use of microarray technology coupled with PCR/isothermal amplification. In such a method, a biochip that performs PCR or isothermal amplification is then coupled with a microarray method downstream. The feasibility to spot several hundred detection regions in the microarray technology makes it appealing for multiplex PCR/isothermal amplification. However, similar to most high sensitivity electrophoresis systems, microarray detection also requires the use of a high power spot-excitation source for the fluorophores hence demanding the use of expensive fluorescence excitation and optical detection components (e.g. lasers, CCD, photomultipliers).

From an instrument cost perspective, of the numerous commercially available instruments, qPCR systems (e.g. Applied Biosystems, BioRad, Roche, Eppendorf) are typically several-fold less expensive than electrophoresis (e.g. ABI, Qiagen, Agilent) and microarray systems (e.g. Affymetrix, Molecular Devices, Roche, Tecan) for comparable applications.

Meanwhile, the DNA fragment detection strategy employed in the integrated biochip, methods, and systems described herein enable a much higher degree of multiplexing as compared to traditional qPCR, while only requiring similar inexpensive optics conventionally used in qPCR. The increased fragment detection capability enables the disclosed techniques to identify more organisms/diseases from a single test as compared to the popular and conventional qPCR technology. Thus, embodiments of the invention enable the use of the relatively low-cost instrumentation of qPCR optics while increasing the fragment detection capability by several folds.

Furthermore, certain embodiments of the invention include universal fit Luer taper-type connectors integrated into the surface of the biochip for quick connection while maintaining an air/water-tight seal of reagent pre-filled syringes/cartridges to the biochip.

BRIEF SUMMARY OF THE INVENTION

Embodiments of the invention include a functionally integrated biochip for multiplex genetic identification. The integrated biochip includes a plurality of separation and detection chambers for receiving a sample material that contains a plurality of sets of DNA fragments of different types. Each of the plurality of separation and detection chambers is spaced apart from each of the other chambers, and each of the separation and detection chambers has a set of DNA probe disposed therein. The set of DNA probes disposed in each of the separation and detection chambers differ in type from those disposed in the other chambers.

In some embodiments, the biochip also includes inputs and chambers for receiving a sample matrix of genetic material and reagents needed to conduct a polymerase chain reaction or isothermal amplification of the genetic material to supply the plurality of collections of DNA fragments.

In other embodiments, to minimize operator intervention and to realize a completely closed biochip system, an integrated reagent cartridge coupled to the biochip which stores all required buffers and waste liquid is provided.

In some embodiments, a biochip for multiplex genetic identification is provided. The biochip includes a sample input port to receive a sample containing a plurality of DNA fragments and a plurality of separation and detection chambers in fluid communication with the sample input port. Each of the plurality of separation and detection chambers is spaced apart from the other chambers, and each chamber contains at least one set of DNA probes immobilized therein. The set of DNA probes in each chamber differs from the sets of DNA probes in the other chambers.

In other embodiments, the biochip includes a wash buffer input port to receive a wash buffer. The wash buffer input port is in fluid communication with the plurality of separation and detection chambers.

In some embodiments, the biochip also includes an amplification chamber to amplify the plurality of DNA fragments. The amplification chamber is in fluid communication with the sample input port and the plurality of separation and detection chambers. In some embodiments, the biochip includes an elution buffer input port to receive an elution buffer and a sample preparation chamber in fluid communication with the elution buffer input port, the sample input port, and the amplification chamber. In other embodiments, the biochip includes a sample preparation wash buffer input port to receive a sample preparation wash buffer and a sample preparation chamber in fluid communication with the sample preparation wash buffer input port, the sample input port, and the amplification chamber. In other embodiments, the biochip includes a post-amplification buffer input port to receive a post-amplification buffer and a post-amplification vent chamber in fluid communication with the post-amplification buffer input port and the amplification chamber. In some embodiments, the biochip includes a post-amplification vent chamber in fluid communication with the amplification chamber and the plurality of separation and detection chambers. In other embodiments, the biochip also includes a waste output port in fluid communication with the plurality of separation and detection chambers.

In some embodiments, the biochip includes a plurality of vent chambers. Each vent chamber is in fluid communication with its corresponding chamber of the plurality of separation and detection chambers.

In other embodiments, the biochip includes at least one background reference chamber not in fluid communication with the sample input port and the plurality of separation and detection chambers. The at least one background reference chamber and at least one of the plurality separation and detection chambers are composed of a same material. In some embodiments, each of the at least one background reference chamber contains at least one DNA probe identical to the at least one DNA probe of its corresponding separation and detection chamber.

In some embodiments, the plurality of separation and detection chambers are connected in parallel. In alternative embodiments, the plurality of separation and detection chambers are connected in series.

In other embodiments, the biochip includes at least one flow gate to control fluid flow between the sample input port and at least one of the plurality of separation and detection chambers.

In some embodiments, the at least one flow gate has an inlet channel and an outlet channel. The at least one flow gate inhibits fluid flow from the inlet channel to the outlet channel with an absence of fluid pressure and permits fluid flow from the inlet channel to the outlet channel with fluid pressure.

In alternative embodiments, the at least one flow gate has an inlet channel and an outlet channel. The at least one flow gate inhibits fluid flow from the inlet channel to the outlet channel with pneumatic pressure and permits fluid flow from the inlet channel to the outlet channel with an absence of pneumatic pressure.

In some embodiments, the biochip includes a plurality of transition channels in fluid communication. Each of the plurality of transition channel has an increasing cross-sectional area in a direction to its corresponding separation and detection chamber.

In other embodiments, the biochip includes a waste output port in fluid communication with the plurality of separation and detection chambers.

In some embodiments, a flow gate is provided. The flow gate includes a first port and a second port separated by a junction, each port being a small chamber at an end of a channel. The flow gate also includes a thin flexible material adhered across the first and second ports. The flow gate has an open configuration and a closed configuration, wherein pressure applied to the thin flexible material changes between the open configuration and the closed configuration. The open configuration has space between the thin flexible membrane and the junction and permits fluid flow between the two channels through the ports, and the closed configuration has the thin flexible membrane in contact with the junction and inhibits fluid flow between the two channels.

In some embodiments, the thin flexible material is plastic.

In some embodiments, the pressure applied to the thin flexible material is pneumatic pressure.

In some embodiments, the flow gate includes at least one layer of material disposed above the ports.

In some embodiments, the flow gate is in the open configuration without the pressure, and the pressure changes the flow gate from the open configuration to the closed configuration.

In other embodiments, the flow gate is in the closed configuration without the pressure, and the pressure changes the flow gate from the closed configuration to the open configuration.

BRIEF DESCRIPTION OF THE SEVERAL
VIEWS OF THE DRAWINGS

FIG. 19A lists examples of forward primers, reverse primers, and probe sequences of organisms. FIG. 19A discloses SEQ ID NOS 2-13, respectively, in order of appearance.

FIG. 19B lists examples of common quencher sequences with dye-quenching moieties according to an embodiment of the invention. FIG. 19B discloses SEQ ID NOS 14-15, respectively, in order of appearance.

Figure 20:
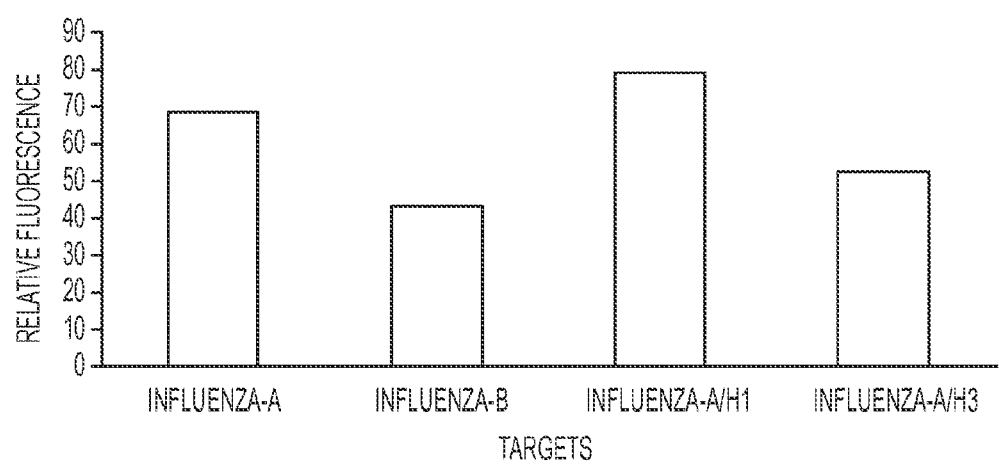

FIG. 20 illustrates increases in relative fluorescence for four tested targets according to an embodiment of the invention.

DETAILED DESCRIPTION OF THE
EMBODIMENTS

Embodiments of the invention detect, by fluorescence, multiple DNA targets of similar or different size within a biochip by separating the DNA fragments into designated chambers in the biochip. Herein, this DNA analysis method is termed "space separation and detection". Using the space separation and detection method offers several key advantages that are not offered by routinely used DNA detection methods such as electrophoresis, mass spectroscopy, qPCR, etc. Embodiments of the invention include an integrated biochip that is capable of accepting a raw sample (such as blood, saliva, urine, swabs) to process via cell lysis, DNA extraction, DNA purification, PCR or isothermal amplification of purified DNA, post-amplification fragment preparation, and, finally, space separation in designated chambers. All processes are performed on a single use disposable integrated biochip capable of "sample-to-results" for research and clinical diagnostics.

Figure 1:
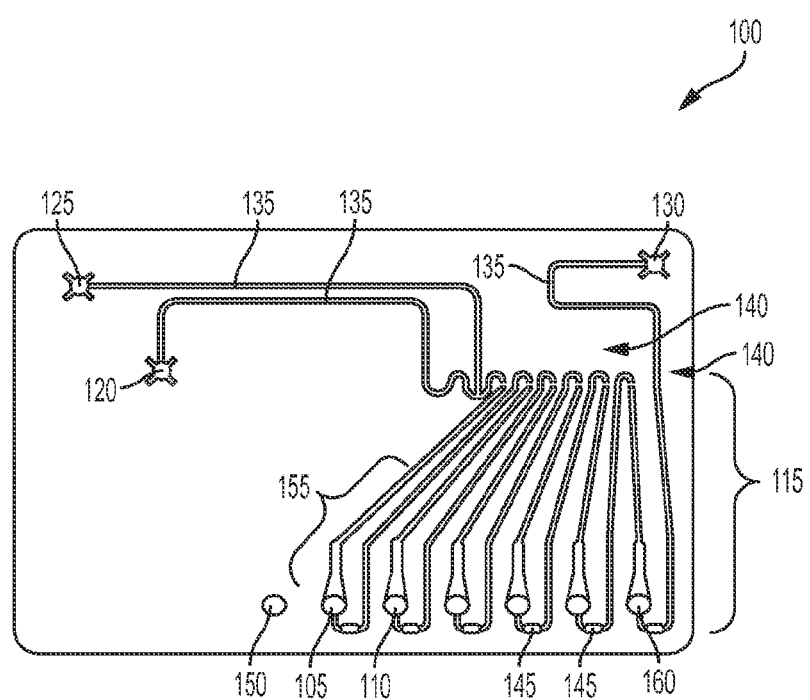
FIG. 1 illustrates a biochip that includes separation and detection chambers and a serial flow path according to an embodiment of the invention.

FIG. 1 illustrates a biochip 100 that includes separation and detection chambers 105, 110 and a serial flow path 115 according to an embodiment of the invention. The biochip 100 also includes a sample input port 120, a wash buffer input port 125, and a waste output port 130. Channels 135 connect the various features of the biochip 100. Flow gates 140 and vent chambers 145 control fluid flow through the channels 135. The biochip 100 also includes a reference chamber 150, discussed in more detail below.

Biochip 100 is configured to receive a sample that contains a collection of DNA fragments, sequentially capture one or more sets of DNA fragments in the separation and detection chambers 105, 110 (and others), and enable detection of the various fragments. The sample to be analyzed is introduced via the sample input port 120 and flows through one of the channels 135 to a flow gate 140 that controls access to separation and detection chamber 105. Upon opening the flow gate to separation and detection chamber 105, the sample mixture flows into chamber 105 under pressure applied at sample input port 120. The vent chamber 145 immediately downstream of chamber 105 permits gas present in the channels upstream of chamber 105, and in chamber 105 itself, to be vented outside of the biochip. The structure and operation of the flow gates and vent chambers are described in more detail below.

Separation and detection chamber 105 is immediately preceded by a transition channel 155. The transition channel expands the cross-sectional area of the channel exiting the flow gate to more closely match the entrance to the chamber 105. The transition channel 155 may be configured to expand the cross-sectional area in a stepwise manner, as shown in the figure, or it may be configured to do so in a continuous manner. Moreover, although only three distinct sections of the transition channel 155 are shown in the figure, other numbers of sections are within the scope of the invention.

In an illustrative implementation, each sequential section of the transition channel 155 increases the cross-sectional area of the channel about two to four times relative to the preceding channel. Other ratios may be employed. By gradually increasing the cross-sectional area of the channel leading to the separation and detection chamber 105, a sudden transition from a relatively narrow passage to a relatively large chamber is avoided. This, in turn, reduces or avoids the occurrence of gas bubbles forming in the chamber 105. By reducing or eliminating gas bubbles in chamber 105, the design of the biochip 100 enables detection errors to be reduced or eliminated, thereby providing relatively higher quality results than without such features.

Figure 2:
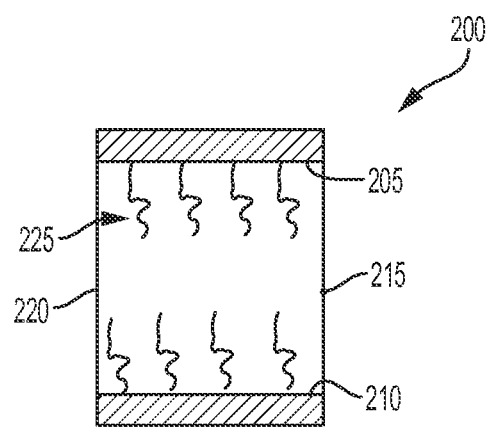
FIG. 2 illustrates a single type of probe immobilized within a separation and detection chamber according to an embodiment of the invention.

As will be described in more detail in connection with FIG. 2, certain steps are taken to retain one or more of the DNA fragments in the separation and detection chamber 105 before passing the sample into a separation and detection chamber 110. In order to pass the sample mixture from chamber 105 into chamber 110, the flow gates 140 upstream of chamber 110 are opened, and the sample mixture flows, under pressure from the sample input port 120, into chamber 110. As described above, a vent chamber 145 immediately downstream of chamber 110 permits gas in the channels and the chamber 110 to escape. Also as before, certain steps are taken to retain one or more of the DNA fragments in the separation and detection chamber 110 before passing the sample into subsequent separation and detection chambers following the same basic procedure as described above.

After passing the sample mixture into separation and detection chamber 160 and performing the steps needed to retain one or more of the DNA fragments of the sample mixture in chamber 160, the flow gate immediately downstream of the chamber 160 is opened, along with all flow gates preceding chamber 160, to permit introduction of a wash buffer fluid through the wash buffer input port 125. The wash buffer fluid passes through all of the separation and detection chambers and exits via the waste output port 130. The flow of wash buffer fluid through the chambers reduces the amount of sample mixture remaining in the separation and detection chambers with the exception of the DNA fragments that have been bound within the chambers. Although biochip 100 is shown as having six separation and detection chambers, more or fewer chambers may be included and remain within the scope of the invention.

As mentioned above, certain steps are taken to retain one or more DNA fragments in the various separation and detection chambers. In an illustrative implementation of the invention, a set of DNA probes are immobilized within each separation and detection chamber. As used herein, a DNA probe is an agent that binds directly to a predefined sequence of nucleic acids. In general, DNA probes can be labeled or unlabeled, as described herein. FIG. 2 illustrates a single type of probe immobilized within a separation and detection chamber 200 according to an embodiment of the invention. FIG. 2 shows a cross-section of one of the chambers (e.g., any of chambers 105, 110, or the others shown in FIG. 1). The chamber 200 has a top surface 205, a bottom surface 210 and sidewalls 215 and 220. Techniques for forming the chamber 200 are discussed in greater detail below. In general, however, a void is created in a substrate to form the sidewalls 215, 220.

In some implementations, the top surface 205 is part of the substrate into which the chamber 200 is formed. In other implementations, bottom surface 210 is part of the substrate. In still further implementations, top surface 205 and bottom surface 210 are formed of a plastic and/or glass material. Using glass as an illustrative example, a set of DNA probes 225, all of the same type, are immobilized onto a glass slides (~1 mm thick). One glass slide is mated and sealed above the chamber 200 to form the top surface 205 and another glass slide is mated and sealed below the chamber 200 to form the bottom surface 210, thereby creating a visual detection window. Thus, in the embodiment shown in FIG. 2, the binding locations for the DNA probes 225 are located on the "roof" and "floor" of the chamber. Although not shown, DNA probes can be immobilized on sidewalls 215, 220 in addition to or in place of those immobilized on the top and bottom surfaces.

One of many illustrative techniques for immobilizing the DNA probes onto the glass slide follows. In some embodiments, desalted 3-prime or 5-prime amine-modified oligonucleotide probes are used. The DNA probe material is first mixed in an immobilization buffer (e.g., 300 nM sodium phosphate (pH 8.0), Polysorbate 20 0.005%, and sarkosyl 0.001%) at a concentration of about 20 µM. A drop of the immobilization buffer solution that is about the size of the detection chamber (e.g., 3.5 mm) or several small droplets (e.g., 0.2 mm or smaller) within a space that is roughly the size of the detection chamber, are made on the glass slide using a micropipette or other robotic dispensing instruments. The glass slide is kept in a humidified chamber (e.g., 50% relative humidity) for few to several minutes (e.g., up to 30 minutes) and then soaked in a deactivation buffer (e.g., 50 nM ethanolamine in 50 nM sodium borate solution of pH 9.0) for about 30 minutes to 1 hour. The deactivation buffer ensures that any region that does not have an immobilized probe(s) is made relatively chemically inert to reduce the likelihood of DNA material adhering to those regions during the probe-DNA interaction. Finally, the glass is rinsed with deionized water for about 1 minute. The glass slide is then affixed to the substrate above the separation and detection chamber(s).

The above technique is merely illustrative, and other known methods for immobilizing probes may be used. In addition, the process set forth above can be used to immobilize DNA probes on the sidewalls of the chambers. The probes can be immobilized to particles (e.g., magnetic beads of 10 nm to 10 µm) and can be placed inside the separation and detection chamber(s) instead of the glass coating method described above. For example, if magnetic particles with immobilized probes were used, a magnet can be energized above and/or below the chamber to retain the magnetic particles during fluid flow.

Referring again to FIG. 1, the biochip 100 also includes a background reference chamber 150. Chamber 150 is formed in the same manner and with the same materials as separation and detection chambers 105, 110, and the other chambers. However, chamber 150 is isolated from the path taken by the sample mixture and, in some embodiments, does not contain any immobilized DNA probes. Thus, any background fluorescence caused by the materials that form the top surface, bottom surface, and sidewalls can be detected. This background fluorescence can then be subtracted from the fluorescence from the separation and detection chambers in order to improve accuracy of the test results.

In other embodiments, one or more DNA probes of the type(s) used in the separation and detection chambers are immobilized in chamber 150. Thus, any background fluorescence caused by the DNA probes, in addition to that contributed by the materials of construction, can also be detected and subtracted from final test results. Further still, other implementations more than one background reference chamber is included in biochip 100. For example, biochip 100 can include one background reference chamber corresponding to each separation and detection chamber (105, 110, and the other) present in biochip 100. In such an embodiment, each of the background reference chambers includes the same type and concentration of immobilized DNA probes present in the corresponding separation and detection chamber. Thus, any variability of background fluorescence due to the different DNA probes can be detected and accounted for.

The visual detection window created by this configuration enables the detection and quantification of fluorescence (for techniques using fluorescent labels or PCR primers) from the DNA probe/target sequence pair from either above or below the surface of the biochip. Furthermore, the use of glass in the structure is advantageous as it is optically clear, has better binding chemistries for the probes, and has low auto-fluorescence compared to most plastics. However, it is understood that the use of plastics in place of glass remains within the scope of the invention.

Figure 3:
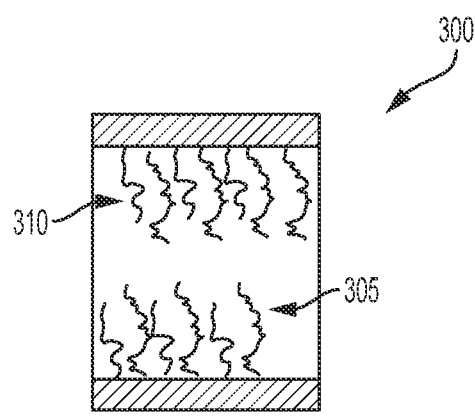
FIG. 3 illustrates more than one type of probe immobilized within a separation and detection chamber according to an embodiment of the invention.

FIG. 3 Illustrates more than one type of probe immobilized within a separation and detection chamber 300 according to an embodiment of the invention. Chamber 300 shares similar features to the chamber 200 of FIG. 2. However, chamber 300 has two types of DNA probes immobilized within the chamber. DNA probes 305 and 310 each bind to different predefined sequences of nucleic acids. Thus, during the separation phase, described in more detail below, two different DNA fragment targets are retained in chamber 300.

Figure 4:
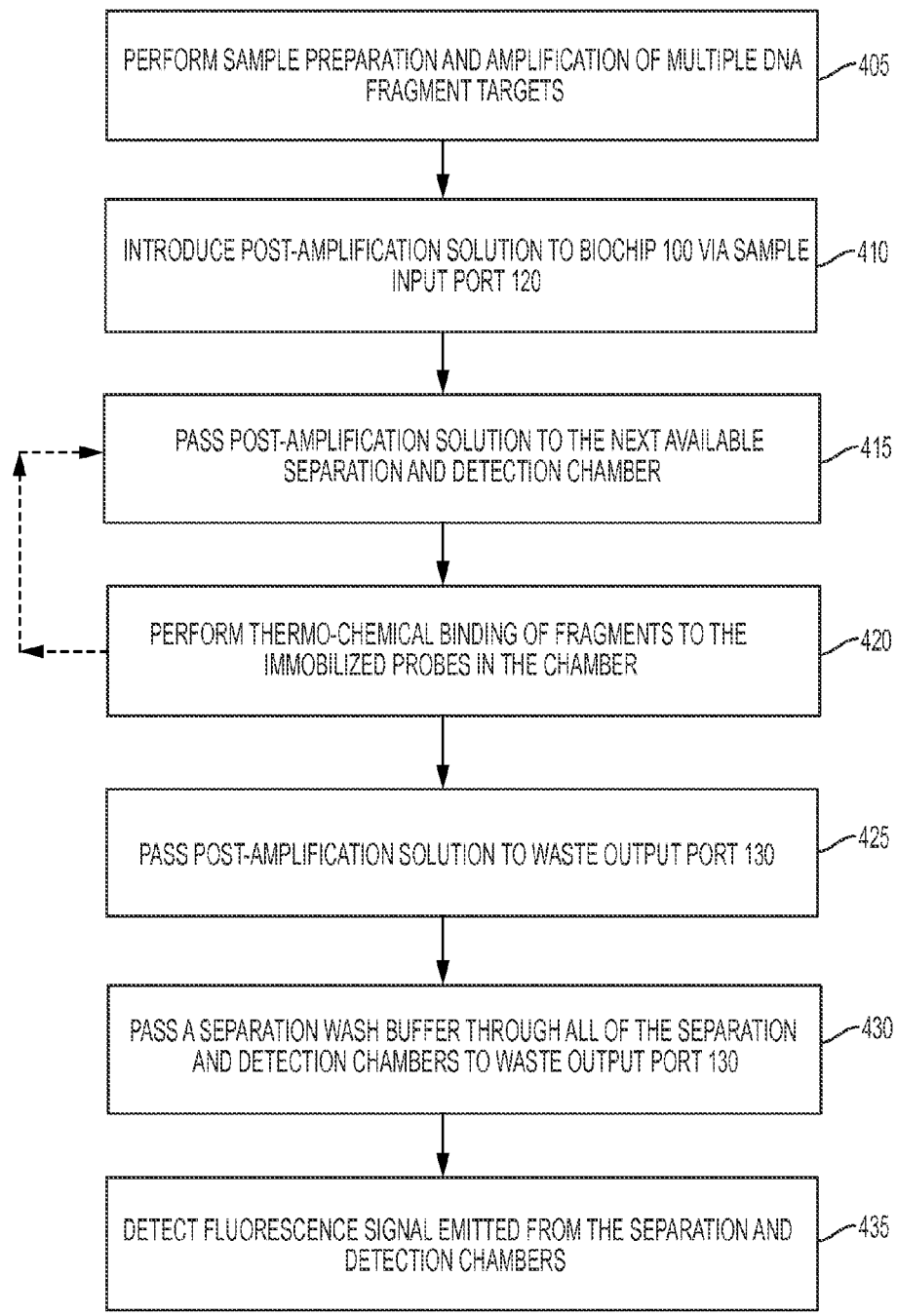
FIG. 4 is a flowchart illustrating a series of steps for using the biochip shown in FIG. 1 according to an embodiment of the invention.

FIG. 4 is a flowchart illustrating a series of steps for using the biochip shown in FIG. 1 according to an embodiment of the invention. Initially, a sample (e.g., blood, saliva, etc.,) is gathered and prepared to create a collection of target DNA fragments using techniques known to one having ordinary skill in the art. The DNA fragments are then amplified using PCR or other DNA amplification techniques such as isothermal amplification (step 405). The particular amplification process and reagents used are determined in part by the nature of the DNA probes immobilized in the separation and detection chambers (105, 110, and the others) as well as the intended process for detecting the presence of the DNA targets.

For example, the PCR/isothermal process can produce amplified DNA fragments that are fluorescently labeled, which, when captured by the immobilized DNA probes, cause the fluorescence that is ultimately detected. In other implementations, the DNA probes include a fluorescent label and the amplified DNA fragments are not labeled. A quencher compound is included in the sample mixture along with the DNA fragments that are passed to the separation and detection chambers. When the DNA target fragments bind to the probes, the fluorescence of those probes is preserved, while the fluorescence of any DNA probes without bound DNA targets is quenched. Thus, in such embodiments, the probes cause the fluorescence that is ultimately detected. A more detailed description of the various illustrative complementary configurations of DNA probes, PCR/isothermal amplification processes, and detection techniques that can be used in biochip 100 are set forth in the incorporated application and references included in the appendix.

For illustrative purposes in connection with the process set forth in FIG. 4, six different types of DNA fragments (fragments types 1-6 herein) are amplified, and the DNA fragments produced by the PCR/isothermal amplification process (step 405) are fluorescently labeled with the same fluorescent label (e.g., green dye FAM). Also for the purpose of this example, each of the six separation and detection chambers (105, 110, and the others) has a different DNA probe immobilized therein that are complementary to the six different types of DNA fragments. After the amplification process, the collection of DNA fragments and any reagents or buffers that are added after amplification is complete (collectively called "post-amplification solution") are introduced to biochip 100 via the sample input port 120 (step 410). As described in greater detail above, one or more flow gates are opened to permit the post-amplification solution to pass into the desired features of the biochip 100.

Next, the post-amplification solution, containing the collection of six different types of DNA fragments, is passed to the next available separation and detection chamber (step 415), which at this point in the process is the first chamber 105. The contents of the first chamber 105 are then subject to a thermo-chemical process to bind fragments of type 1 to the immobilized DNA probes in the first separation and detection chamber 105 (step 420). After the binding process is complete, the post-amplification solution is passed to the next available separation and detection chamber (repeat step 415), which is now chamber 110. Again, a thermo-chemical binding process is performed to capture DNA fragments of type 2, which are complementary to the DNA probes in the second separation and detection chamber 110, within the second chamber (repeat step 420).

Steps 415 and 420 are repeated until the post-amplification solution has passed into each of the six separation and detection chambers and each of the six different types of DNA fragments have been bound to the DNA probes to which they correspond. After the final binding step (step 420), the remaining post-amplification solution is passed to waste output port 130 (step 425). The illustrative process next passes a separation wash buffer, which is introduced via wash buffer input port 125, through all of the separation and detection chambers to waste output port 130 (step 430). The wash buffer removes unbound DNA fragments from the separation and detection chambers.

Finally, the fluorescence of the six separation and detection chambers 105, 110, and the others (and, optionally, the background reference chamber 150) are detected and quantified (step 435). Any of the equipment for and methods of detecting and quantifying the fluorescence known to one having ordinary skill in the art can be used during this step. For example, use of fluorometers appropriate for use in Quantitative PCR (qPCR) techniques are within the scope of the invention. Because each separation and detection chamber 105, 110, and the others had a different DNA probe immobilized therein, each chamber captured a different type of DNA fragment. Thus, embodiments of the invention enable one to use the same fluorescent label for each of the plurality of different DNA types in the sample without the problem of being unable to distinguish between the various DNA types.

Figure 5:
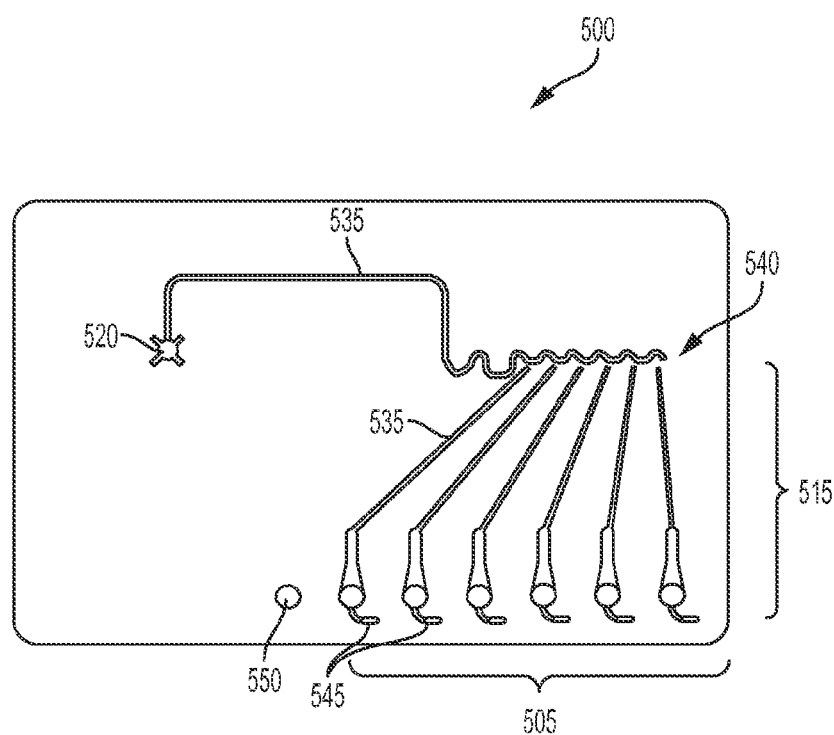
FIG. 5 illustrates a biochip that includes separation and detection chambers and a parallel flow path according to an embodiment of the invention.

FIG. 5 illustrates a biochip 500 that includes separation and detection chambers 505 and a serial flow path 515 according to another embodiment of the invention. The biochip 500 also includes a sample input port 520 and channels 535 connect the various features of the biochip 500. Flow gates 540 and vent chambers 545 control fluid flow through the channels 535. The biochip 500 also includes a reference chamber 550, discussed in more detail above.

Biochip 500 is similar in many respects to the biochip 100 described in detail above. However, biochip 500 is configured to receive the post-amplification solution and distribute the solution among six channels that form parallel flow paths 515 in contrast to the serial flow path 115 of biochip 100. In this context, "parallel flow" means that the sample solution passes into a particular separation and detection chamber 505 without having passed through any other separation and detection chamber 505. In this regard, the channels that form the flow paths need not be strictly geometrically parallel (as shown in FIG. 5A and FIG. 5B), however, the paths can be geometrically parallel. In addition, it is understood that the post-amplification solution need not enter the channels or the separation and detection chambers 505 at exactly the same time.

The sample to be analyzed is introduced via the sample input port 520 and flows through the channels 535 to flow gates 540 that control access to separation and detection chambers 505. Upon opening the flow gates to the multiple separation and detection chambers 505, the sample mixture flows into chambers 505 under pressure applied at sample input port 520. The vent chambers 545 immediately downstream of chambers 505 permit gas present in the channels upstream of chambers 505, and in the chambers 505 themselves, to be vented outside of the biochip. The structure and operation of the flow gates and vent chambers are described in more detail below.

Separation and detection chambers 505 include DNA probes therein. However, unlike the serial embodiment of the biochip 100, it is not required that the DNA probes be immobilized in the chambers 505 because the portion of post-amplification solution that enters each of the chambers 505 does not leave the chamber. Although not required, it is understood that in some implementations of the parallel flow embodiment of biochip 500, one or more DNA probes may be immobilized in the chambers 505 using the techniques described above.

Another difference between the serial flow biochip 100 and the parallel flow biochip 500 is that the step of binding the desired DNA fragments of the sample to the probes in the multiple chambers 505 need not happen in sequence. Rather, all of the separation and detection chambers 505 can be subjected to a process for binding the desired DNA fragments to the DNA probes in the same set of steps. In the alternative, one or more of the chambers 505, but less than all chambers, can be subjected to a binding process at the same time. For example, a first set of three chambers can be subjected to a thermo-chemical binding process during a first set of binding steps, while the remaining three chambers can be subjected to the same or similar set of binding steps after the first set of binding steps is completed. Although biochip 500 is shown as having six separation and detection chambers, more or fewer chambers may be included and remain within the scope of the invention.

Figure 6:
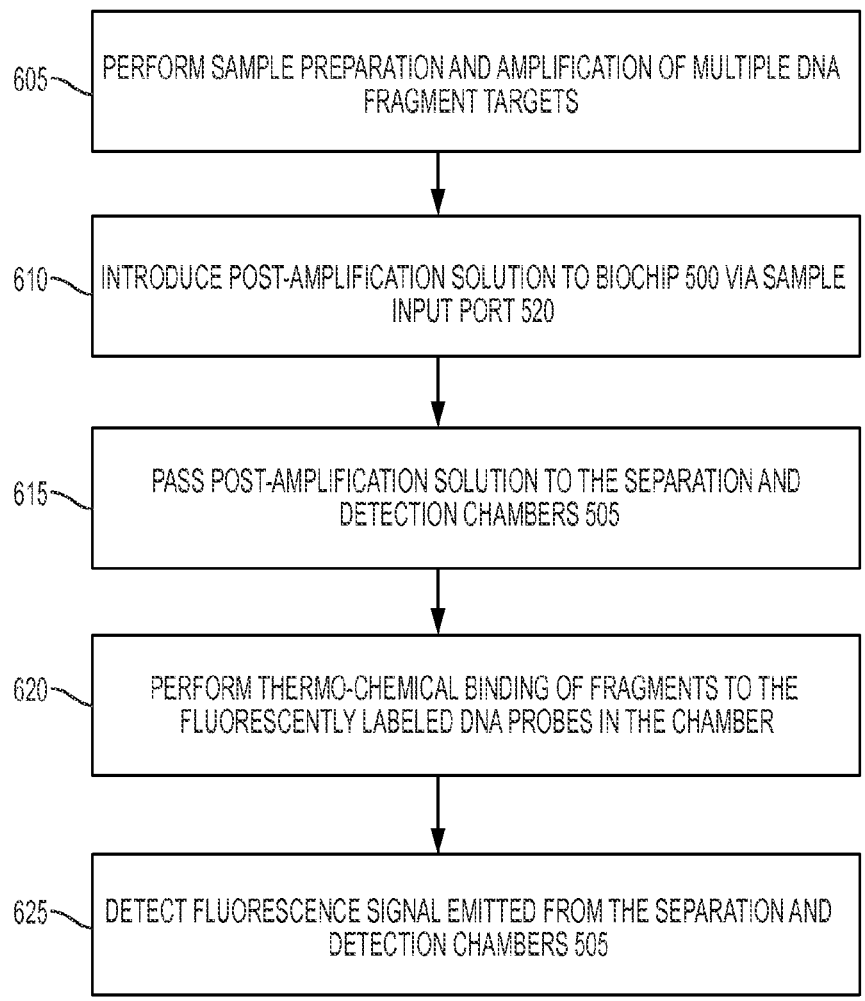
FIG. 6 is a flowchart illustrating a series of steps for using the biochip shown in FIG. 5 according to an embodiment of the invention.

FIG. 6 is a flowchart illustrating a series of steps for using the biochip 500 shown in FIG. 5 according to an embodiment of the invention. As with the process for using biochip 100, a sample is gathered and prepared to create a collection of target DNA fragments using techniques known to one having ordinary skill in the art and the DNA fragments are then amplified using PCR or other DNA amplification techniques (e.g., isothermal amplification) (step 605). As before, the particular PCR/isothermal amplification process and reagents used are determined in part by the nature of the DNA probes present in the separation and detection chambers 505 as well as the intended process for detecting the presence of the DNA targets.

For illustrative purposes in connection with the process set forth in FIG. 6, six different types of DNA fragments (fragments types 1-6 herein) are amplified (step 605). However, unlike the process previously described, the DNA fragments produced by the PCR or isothermal amplification process (step 605) are not fluorescently labeled. Rather, the DNA probes present in the chambers 505 are labeled with a fluorescent label at either the 3-prime end or 5-prime end of the probe. Meanwhile, the unlabeled ends of the DNA probes have quenchers thereon. The opposing ends of the DNA probes have a number of bases that are complementary to each other. Also for the purpose of this example, each of the six separation and detection chambers 505 has a different type of DNA probe present therein that is complementary to one of the six different types of DNA fragments. After the amplification process, the collection of DNA fragments and any reagents or buffers that are added after amplification is complete (collectively called "post-amplification solution") are introduced to biochip 500 via the sample input port 520 (step 610). As described in greater detail above, one or more flow gates are opened to permit the post-amplification solution to pass into the desired features of the biochip 500.

Next, the post-amplification solution, containing the collection of six different types of DNA fragments, is passed to the separation and detection chambers 505 (step 615). The contents of the chambers 505 are then subject to a thermochemical process to bind each type of DNA fragment to its complementary type of DNA probe (step 620). In this embodiment, when a DNA fragment binds to its complementary DNA probe, the fluorescence of the probe is maintained. Any DNA probes in any of the chambers 505 that are not bound to a complementary DNA fragment will self-quench via the complementary bases at the 3-prime and 5-primes ends binding to each other.

After the binding process is complete, the fluorescence of the six separation and detection chambers 505 (and, optionally, the background reference chamber 550) are detected and quantified (step 625). As mentioned above, any of the equipment for and methods of detecting and quantifying the fluorescence known to one having ordinary skill in the art can be used during this step. Because each of the separation and detection chambers 505 had a different DNA probe therein, each chamber detects a different type of DNA fragment.

Figure 7:
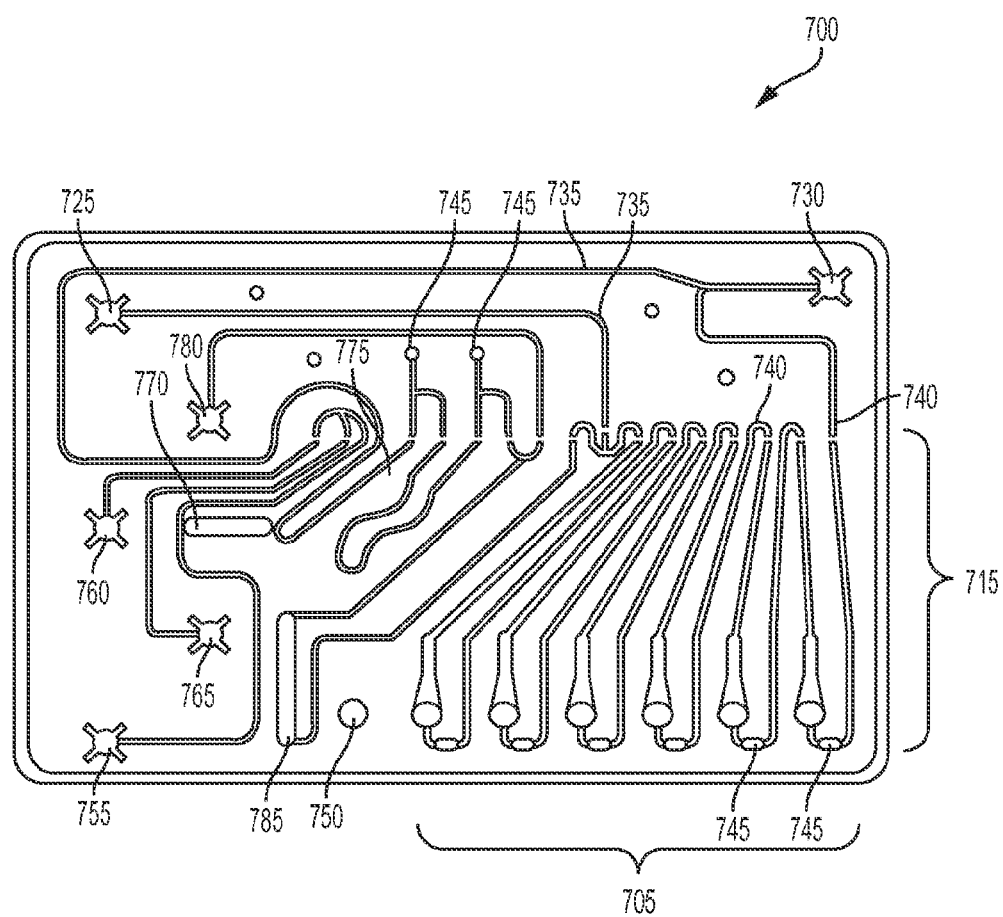
FIG. 7 illustrates an integrated biochip that includes sample preparation, target separation, and target detection features according to an embodiment of the invention.

FIG. 7 illustrates an integrated biochip 700 that includes sample preparation, target separation, and target detection features according to an embodiment of the invention. The biochip 700 includes a serial flow path 715 leading through separation and detection chambers 705 that is similar to that of the biochip 100. However, other embodiments include a parallel flow path such as the one described above. The biochip 700 includes a wash buffer input port 725, a waste output port 730, connecting channels 735, flow gates 740, vent chambers 745, and a reference chamber 750. These features have similar characteristics and operate in a similar manner to the corresponding features described in connection with the biochip 100 and biochip 500.

Biochip 700 is similar in many respects to the biochip 100 described in detail above. However, biochip 700 has additional features that enable sample preparation and PCR/isothermal amplification to be performed on the biochip 700. Thus, the biochip 700 also includes a sample input port 755, a sample preparation wash buffer input port 760, an elution buffer input port 765, and a sample preparation chamber 770. As described in more detail below, these additional features are used to prepare a sample material for PCR/isothermal amplification. The biochip 700 further includes an amplification chamber 775, a post-amplification buffer input port 780, and a post-amplification vent chamber 785. These later features enable PCR/isothermal amplification to be performed on the biochip 700. Other embodiments of the biochip includes some, but not all, of the components listed above.

The sample input port 755 permits a sample matrix (e.g., blood, saliva, urine, swab material) to be introduced into the sample preparation chamber 770. Similarly, the sample preparation wash buffer input port 760 permits a sample preparation wash buffer to be introduced into the sample preparation chamber 770, and the elution buffer input port 765 permits an elution buffer to added to the mixture in the sample preparation chamber 770. After the steps needed to liberate the target DNA fragments are performed on the sample matrix and reagents in the sample preparation chamber 770, the mixture is introduced into the amplification chamber 775.

After PCR thermocycling is conducted, a post-amplification buffer is introduced to the amplification chamber 775 via the post-amplification buffer input port 780, and the combined solution is passed to the post-amplification vent chamber 785. The post-amplification vent chamber is similar to other vents of the biochips described herein in that it permits gases in the upstream channels as well as the chamber itself to escape while retaining the sample solution. Fluid flow between the sample preparation and PCR amplification features is achieved via the same techniques set forth in more detail above. Generally, flow gates 740 control the flow of fluid between the various features, and vent chambers 745 permit gas to be purged from the chambers and the connecting channels.

The sample to be analyzed is then introduced to the separation and detection chambers 705 in a manner similar to the one set forth in connection with the biochip 100. As mentioned above, alternative embodiments of the biochip 700 include a parallel flow path. In such embodiments, the post-amplification solution generated by the "front-end" of biochip 700 passes into the separation and detection chambers in a manner similar to the one provided above in connection with the biochip 500.

Figure 8:
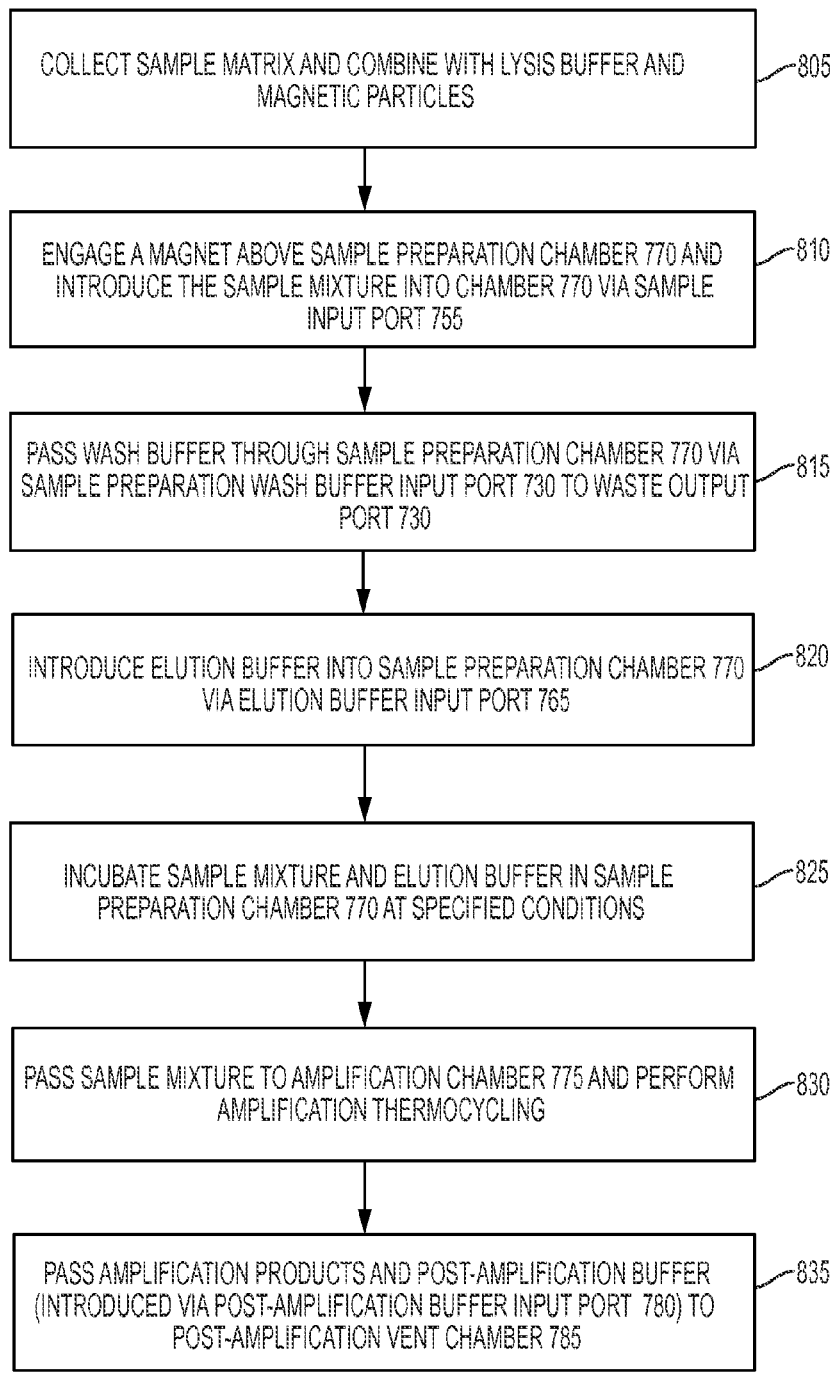
FIG. 8 is a flowchart illustrating a series of steps for using the biochip shown in FIG. 7 according to an embodiment of the invention.

FIG. 8 is a flowchart illustrating a series of steps for using the biochip 700 shown in FIG. 7 according to an embodiment of the invention. Initially, a sample matrix is collected (e.g., a patient's blood) and combined with a lysis buffer and magnetic particles (step 805). The lysis buffer gains access to the DNA material inside the blood cells, and the DNA material binds to the magnetic particles under certain conditions. Next, a magnet is engaged above the sample preparation chamber 770, and the sample mixture created in step 805 is passed into the sample preparation chamber 770 via sample input port 755 (step 810). A sample preparation wash buffer is introduced to the sample preparation chamber 770 via the sample preparation wash buffer input port 760 and passed through the chamber 770 to the waste output port 730 (step 815). This wash step removes unwanted material and contaminants (e.g., cellular debris) from the sample mixture. However, the desired DNA material remains in the sample preparation chamber 770 because the material is bound to the magnetic particles, which are held within the sample preparation chamber 770 via the magnet engaged above.

Next, an elution buffer is added to sample preparation chamber 770 via the elution buffer input port 765 (step 820). The sample mixture and elution buffer are incubated in the sample preparation chamber 770 at the appropriate conditions (e.g., 50 deg C. for 3 minutes) (step 825), which would be known to one having ordinary skill in the art. During the incubation step, the elution buffer causes the DNA material to be liberated from the magnetic particles. The washed and eluted sample mixture is then passed into the amplification chamber 775 (step 830), leaving behind the magnetic particles that are still held in the sample preparation chamber 770 by the magnet. The needed amplification reagents can be included in the elution buffer or present in the amplification chamber 775 (or channels leading to the amplification chamber) in lyophilized form. In embodiments employing reverse-transcriptase-PCR (RT-PCR), the RT-PCR reagents are included in the elution buffer and the RT reaction is performed in the sample preparation chamber 770. Meanwhile, the amplification reagents are present in the amplification chamber 775 (or channels leading to the amplification chamber) in lyophilized form. The sample is then subjected to PCR thermocycling or isothermal amplification (830) to amplify the desired target DNA fragments.

After completion of the amplification reaction by thermocycling in case of PCR amplification or by constant temperature in case of isothermal amplification, the amplified products are passed to the post-amplification vent chamber 785 and a post-amplification buffer is introduced via the post-amplification buffer input port 780 into the post-amplification vent chamber 785 (step 835). The amplified products and post-amplification buffer are mixed in the post-amplification vent chamber 785 to form the "post-amplification solution". At this point, the post-amplification solution is passed into the separation and detection chambers 705 in a serial flow fashion following steps 415-430 of FIG. 4 (step 840). Finally, the fluorescence of the six separation and detection chambers 705 (and, optionally, the background reference chamber 750) are detected and quantified. Any of the equipment for and methods of detecting and quantifying the fluorescence known to one having ordinary skill in the art can be used during this step.

Figure 9:
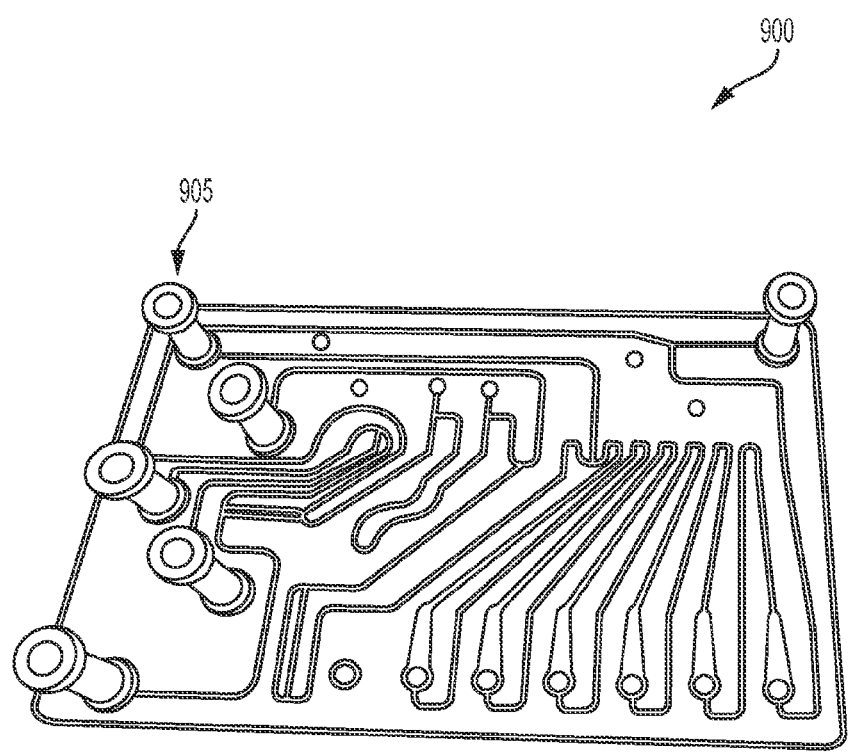
FIG. 9 illustrates an integrated biochip that includes universal LUER-LOK® connections integrated into the biochip according to an embodiment of the invention.
Figure 14A:
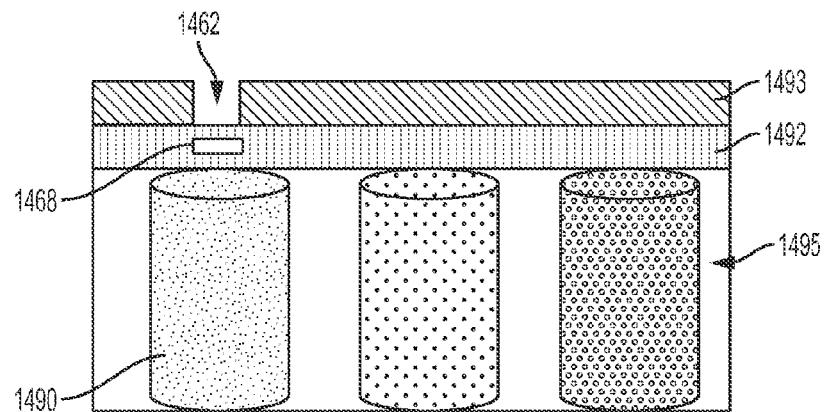
FIG. 14A illustrates a buffer cartridge assembly with a self-sealing rubber gasket according to an embodiment of the invention.
Figure 14B:
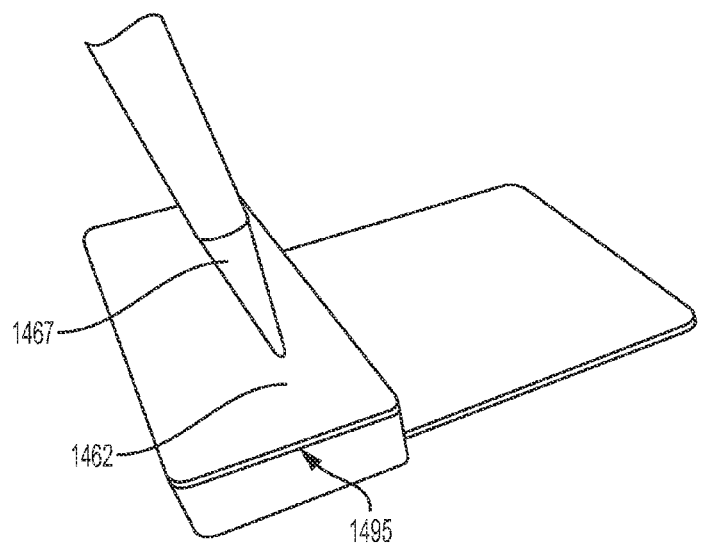
FIG. 14B illustrates inserting a sample to a buffer cartridge according to an embodiment of the invention.

FIG. 9 illustrates an integrated biochip 900 that includes universal LUER-LOK® connections 905 integrated into the biochip according to an embodiment of the invention. In other embodiments, an alternate Luer taper-type connection is used (e.g., a LUER-SLIP®). The LUER-LOK® connectors provide for quick connection between the biochip and the source of materials for use in the biochip while maintaining an air/water-tight seal. Alternatively, a buffer cartridge integrated onto the biochip may be used instead of syringes and LUER-LOK® as shown in FIGS. 14A and 14B.

Certain implementations of the various embodiments of biochips described above include a filter (<50 μm) in or connected to the biochip's waste output port. The filter in the waste output port prevents backflow of material from the waste receptacle (e.g., a syringe) to the biochip when liquid is present in the waste receptacle. Alternatively, a check valve is in or fitted to the waste output port to serve the same purpose of backflow prevention achieved using a filter.

The various implementations of the biochips described herein can be fabricated from a variety of materials including glass, silicone, soft polymers (e.g., PDMS), and plastics. Plastic polymers such as Poly(methyl methacrylate) (PMMA), polypropylene, polycarbonate, polyimide, cyclic olefin copolymers (COC), as well as glass are generally preferred, as those materials have good biocompatibility and are stable at high temperature (>80 C) utilized in bioprocesses. Meanwhile, soft polymers are less desirable as they generally exhibit gas and water permeability, especially at elevated temperatures.

In certain embodiments, the features of the biochips (e.g., channels, wells, chambers, etc.) are fabricated in the underside of a plastic substrate via hot embossing, injection molding, laser machining, or micro-machining process. It is understood that the foregoing list is merely illustrative, and other techniques for forming the biochip features are within the scope of the invention. The plastic substrate with the features is then bonded to a plastic film (of, e.g., ~150 µm thickness) onto the underside to create enclosed channels, chambers, and other features in the biochip. For example, COC can be used as the substrate and thin film in an embodiment of the biochip. After forming the features in the substrate, the thin film and substrate are thermally bound using heat and pressure (e.g., 135° C. at 200 PSI for about 1 minute). In general, the temperature used is close to the glass-transition temperature of the plastic material used. Thus, other temperatures are within the scope of the invention, depending on the materials of construction. In addition, other pressures and times, e.g., ranging from 20 PSI to 1000 PSI and a few seconds to several minutes, respectively, may be used. A device, such as a Model 4398 laboratory press from Carver, Inc. may be used to achieve these conditions.

Another illustrative technique uses heat, pressure, and a solvent to achieve bonding between the substrate and the thin film. In such a process, cyclohexane is applied to the surface of the substrate and/or thin film. The two components are then brought together under about 100 PSI at roughly 70° C. for about 2 minutes. This process produces a biochip which can withstand internal pressures of at least 100 PSI without delaminating.

As shown in FIG. 7, amplification chamber 775 exhibits a meander. One advantage of this feature is that it reduces or eliminates the tendency of the plastic film to deflect inward into the channel that it forms. By reducing or eliminating this deflection, a relatively flatter surface is available for contacting the heating elements used during the PCR thermocycling or isothermal amplification. This provides better temperature control, increased efficiency, and improved performance. In addition, the meander provides for relatively better mixing than a chamber with straight channels.

As set forth above, fluid flow control between the chambers, channels, reservoirs, wells, and other features is controlled in part by flow gates (e.g., flow gates 140 of FIG. 1). These flow gates can be any of a number of valves, flow control features, and the like suitable for use in microfluidic service known to one having ordinary skill in the art. In one illustrative implementation, the small chambers at the end of the channels that form the gate function are about 500 µm in diameter; larger and smaller diameters may also be used.

Figure 10A:
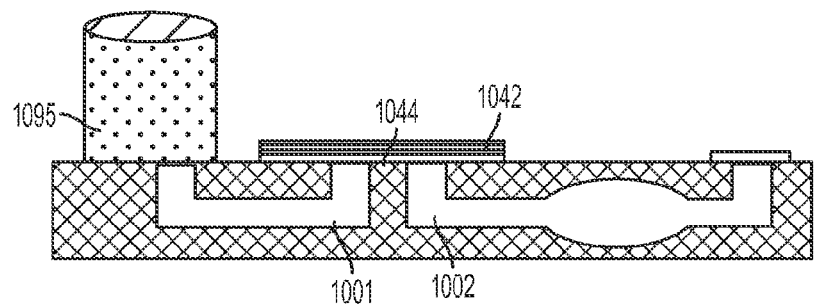
FIG. 10A illustrates a flow gate of an integrated biochip according to an embodiment of the invention.

FIG. 10A illustrates a flow gate mechanism in some embodiments. In these embodiments, a flow gate includes a flexible membrane 1042 and an adhesive 1044 on one side of the membrane 1042. The flexible membrane 1042 is affixed to the area circumscribing the openings of channels 1001 and 1002, and the adhesive 1044 initially seals the area between the two disconnected channels.

Figure 10B:
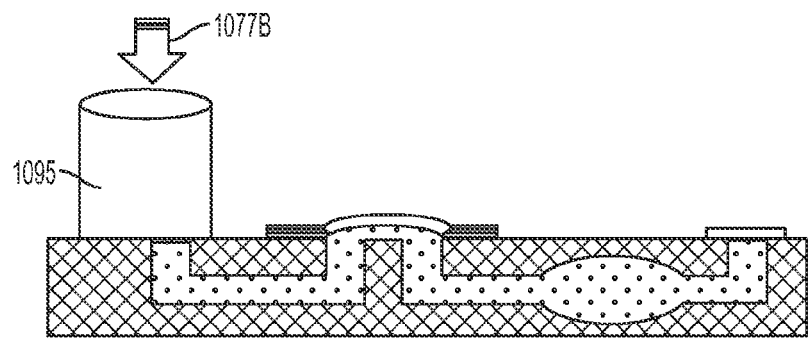
FIG. 10B illustrates an open configuration of the flow gate of FIG. 10A according to an embodiment of the invention.
Figure 10C:
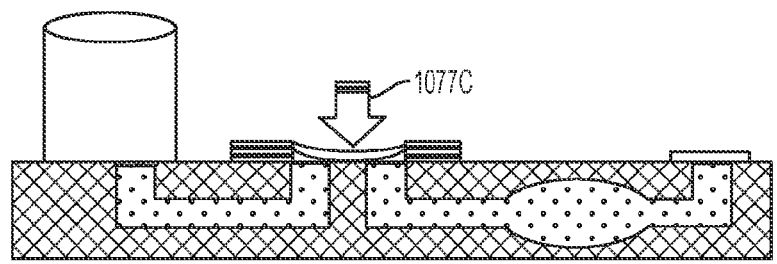
FIG. 10C illustrates a closed configuration of the flow gate of FIG. 10A according to an embodiment of the invention.

Without the seal, fluids in the cartridge may leak or flow into other areas of the biochip because flow-gate membrane does not seal airtight when not connected to an instrument. When the adhesive 1044 is applied, it seals the channel leading to the reservoir (upstream) in the cartridge. However, upon the first use of the biochip on the instrument, the fluid pressure will delaminate the adhesive between 1001 and 1002, breaking the adhesive seal. Once the adhesive 1044 is soiled by the fluid at its first use as shown in FIG. 10B and FIG. 10C, the membrane at that flow gate needs a pneumatic pressure to actuate the membrane either to allow fluid flow in FIG. 10B or to prevent fluid flow in FIG. 10C. Therefore, in some embodiments, the adhesive 1044 replaces a typical sealing mechanism (e.g. foil seal) for each reservoir of the cartridge to prevent fluid from moving out of the reservoir and into other areas of the biochip.

FIG. 10B illustrates an open configuration of the flow gate. Applying pressure 1077B to an end of a channel causes fluid pressure to apply upward pressure to the flow gate membrane 1042. For example, air pressure can be applied from the buffer cartridge 1095 to channel 1001 to the membrane 1042. As a result, the flexible flow gate membrane bends and allows the fluid to flow through a next channel. Because the adhesive 1044 circumscribes the area, the fluid is restricted to stay within the area and flows from one channel to another channel.

FIG. 10C illustrates a closed configuration of the flow gate. The flow gate can be closed by applying pressure 1077C (e.g., 20 PSIG) to the thin flexible material adhered to the gating connector ports in the biochip directly above the flow gate junction. By closing the connection between the two channels of the flow gate, the fluid cannot flow from one channel to another channel. In other embodiments, additional layers of material are disposed above the gating ports to provide channels that pass above the gate junction. Pressure applied to the channels passing above the gate junctions distort the layers of material, thereby closing the flow gate. The fluid gating connectors on the biochip can be controlled by pneumatic pressure between slightly above 0 PSIG and 50 PSIG, but other pressure ranges are within the scope of the invention. In another illustrative implementation, the flow gates are normally closed and are opened by deforming material adjacent to the flow gate in order to open the gate junction.

In another embodiment, pressure applied to the flexible membrane is adjusted to control the flow rate of the fluid. Thus the flexible membrane can be adjusted to a partially open configuration.

Some examples of materials for the flow-gate membrane include PTFE, Teflon, PVC, polyethylene, polypropylene, polyimide, latex, silicone, and nitrile. The thickness can, for example, range from ~5 µm to ~2 mm. The adhesive on the bottom side can be, for example, acrylic adhesive and silicone adhesive. These examples are two common adhesives on the market, but the scope of the invention covers other types of adhesives. In some embodiments, the adhesive are applied to the membrane prior to assembly onto the biochip by a spray method, film deposition method, laminating method, etc. The thickness of the adhesive is optionally kept as thin as possible and ranges between 5 um to 1 mm, for example. In some embodiments, a thin adhesive layer and thin (flexible) membrane configuration is preferred.

The scope of the invention is not restricted to the flow gate as described above. Other types of flow gates that controls the fluid flow between two channels are within the scope of the invention.

In one embodiment, the biochip is mated with an interface and control instrument such that the pneumatic controls are disposed atop the flow gate junctions. Each pneumatic control is individually addressable to control flow fluid across a channel on either side of the flow gate. In one embodiment, the interface and control instrument is configured to open the various flow gates according to a programmed sequence at predetermined times. In another embodiment, an individual using the instruction actuated each flow gate manually. The interface and control instrument can also be equipped with the heaters for sample preparation and PCR or isothermal amplification, reagent and sample input mechanisms, and fluorescent detection devices.

In some implementations, the interface and control instrument also controls the introduction and flow of fluids in the biochip. For example, one embodiment of the control instrument actuates (e.g., via a servo-mechanical device) syringes, filled with a predetermined quantity of liquid, that are attached to the LUER-LOK® connections at the sample input port 755, the sample preparation wash buffer input port 760, and the wash buffer input port 725. Alternatively, a cartridge with pre-filled buffers can be assembled or affixed to the biochip such that the input and output ports in the biochip are mated to the designated prefilled buffers in the cartridge. The buffers can then be pneumatically driven from the cartridge into the designated ports in the biochip. Meanwhile, the elution buffer input port 765 and post-amplification buffer input port 780 are supplied with their corresponding fluids by pneumatic pressure applied to a quantity of fluid. In an illustrative embodiment, pressures under 10 PSIG are used to supply the fluid to ports 765 and 780 (e.g., 0.5 PSIG). However, other pressures are within the scope of the invention.

Any of the steps for using the biochips can be performed as part of an automated process. For example, in one process for using the biochip in a semi-automated fashion, an operator connects a prefilled buffer cartridge or the various syringes and/or LUER-LOK® adapters to the various ports on the biochip. The operator then places the biochip into a chamber that is part of the interface and control instrument. The chamber is designed such that individually addressable pneumatic actuators are disposed above the various flow gates of the biochip. The control instrument then conducts each step of the process up to the point of detecting the fluorescence emitted by the separation and detection chambers. At this point, the operator moves the biochip to another chamber of the interface and control instrument that has one or more optical readers to detect the fluorescence signal. One of skill in the art will understand that this semi-automated process is merely illustrative, and that all steps of the process can be performed in a single chamber, which incorporates all controls, fluid interface connections, and optical readers.

Referring again to FIG. 7, the features of an embodiment of biochip 700 have the following illustrative dimension. In one implementation, the overall biochip size is about 9.9 cm (3.9 inches) by about 7 cm (2.75 inches). The channels 735 that carry the sample matrix and lysis buffer also contains nano and microbeads (<10 µm), cell debris, and/or other sample related material (e.g., plasma, proteins, and/or debris from swabs used during the sample input). Such channels include, for example, the channel from the sample input port 755 to the sample preparation chamber 770 and the channel leading to the waste output port 730. Hence, the dimensions of these channels are about 800 µm by 800 µm. This relatively large channel cross section reduces the likelihood of clogging of the channel when micro-beads or debris aggregate. In other implementations, channel dimensions can be 300 µm to 2000 µm to reduce channel clogging. Larger cross-sectional areas are also within the scope of the invention. Channels which are expected to be generally free from debris, magnetic beads, and/or other particles are about 500 µm by 500 µm. However, larger or smaller dimensions are within the scope of the invention (e.g., 50 µm to 2000 µm and beyond). In the illustrative embodiment, all LUER-LOK® ports are standard size, which enable the ports to accommodate reservoirs, syringes, and/or other Luer taper interface connections that have volume storage capacity from, e.g., 50 µL to 50 mL.

The separation and detection chambers 705 are about 3.5 mm in diameter with a volume of about 40 µL. Such a size will accommodate an optical sensor above the chamber that has an active capture area of 3 mm diameter. The active capture area of the sensor will determine the size of the detection chamber. Thus, other diameters for the separation and detection chambers are envisioned for larger or smaller optical sensors. Providing a chamber that is about 0.5 mm larger in diameter than the active capture area of the sensor provides alignment tolerance between the biochip and the optical sensor.

In the illustrative embodiment of biochip 700, the volume of the amplification chamber 775 is 20 µL. In other implementations, the amplification chamber can be as small as 10 nL to 50 µL. Meanwhile, the volume of the sample preparation chamber 770 is about 20 µL and has a width of about 1300 µm. In this embodiment, the volume of the sample preparation chamber 770 is about the same size of the amplification chamber 775 so that when the nucleic acids are eluted in the sample preparation chamber 770, that volume can be directly passed into the amplification chamber 775.

The post-amplification vent chamber 785 is about 40 µL. In some implementations, the post-amplification vent chamber 785 volume matches that of the separation and detection chambers 705. Thus, upon completion of amplification, the sample volume moves to the post amplification vent chamber 785 and the addition volume accommodates the post amplification buffer solution, which is mixed with the amplification products inside chamber 785. The total volume of post-amplification solution then directly flows into the separation and detection chambers 705.

In an embodiment of the biochip 700 that includes a parallel flow path for the separation and detection chambers 705, the total volume of the post-amplification vent chamber 785 will be roughly equal to or slightly larger than the volume of all of the separation and detection chambers 705 combined. Thus, the post-amplification vent chamber 785 will accommodate the amplified products as well as the needed amount of post amplified buffer to supply a sufficient amount of post-amplification solution to each of the separation and detection chambers 705.

As set forth above, the various vent chambers in biochip 700 enable gas in the channels and chambers upstream of the corresponding vent chamber to be removed from the biochip. Each vent chamber has a membrane affixed to the top and/or bottom of the chamber. The membrane permits the expulsion of gas while retaining liquid during liquid flow in the biochip. The pore size of the membrane is about 0.45 µm. However, the pore size can range from 0.01 µm to 2 µm. Non-limiting examples of materials suitable for use as a vent membrane include Millipore 0.22 µm PTFE membrane material and Millipore SUREVENT® 0.45 µm PVDF membrane material. The vent membranes are bonded to the biochip after bonding the thin film to the substrate and creating holes in the thin film corresponding to the vent chambers. The membranes can be affixed using any number of adhesives known in the art, or the membranes can be joined by thermal welding and/or ultrasonic welding. Membranes attached in this way can withstand an internal pressure of at least 45 PSI. Thus, this permits fluids to be loaded into channels and chambers up to a vent membrane by keeping the fluid loading pressures below this amount (e.g., <10 PSI).

Figure 11A:
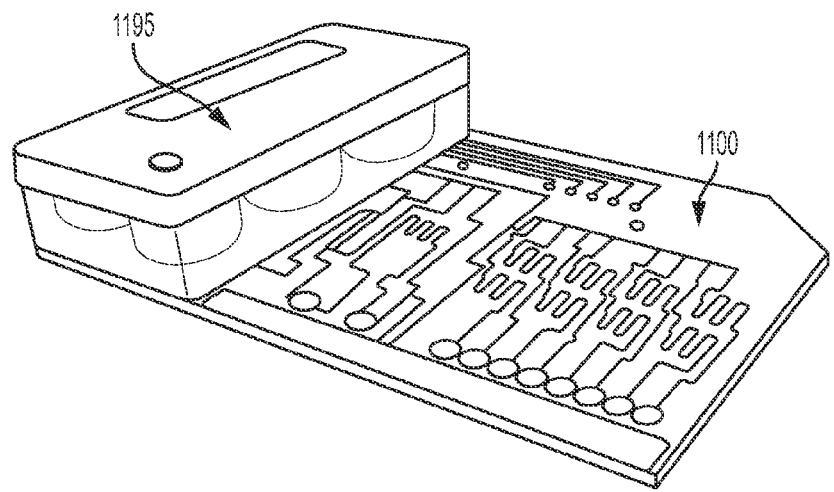
FIG. 11A illustrates an angled view of an integrated biochip with an integrated cartridge according to an embodiment of the invention.
Figure 11B:
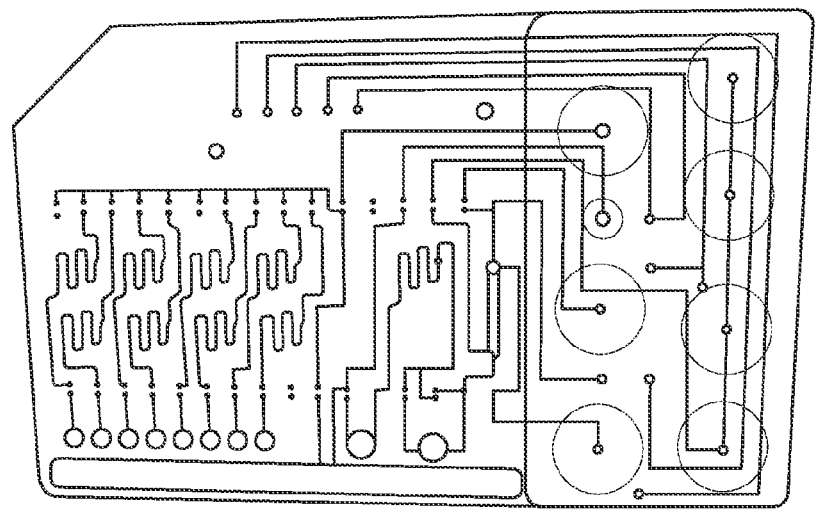
FIG. 11B illustrates a bottom view of the integrated biochip of FIG. 10A according to an embodiment of the invention.

FIGS. 11A and 11B illustrate some embodiments of an integrated biochip system, where an integrated biochip 1100 is connected to an integrated cartridge 1195. FIG. 11A shows an angled view, and FIG. 11B illustrates a bottom view of the integrated biochip 1100. The integrated cartridge contains various reservoirs and provide buffer fluids to their corresponding input ports.

Figure 12:
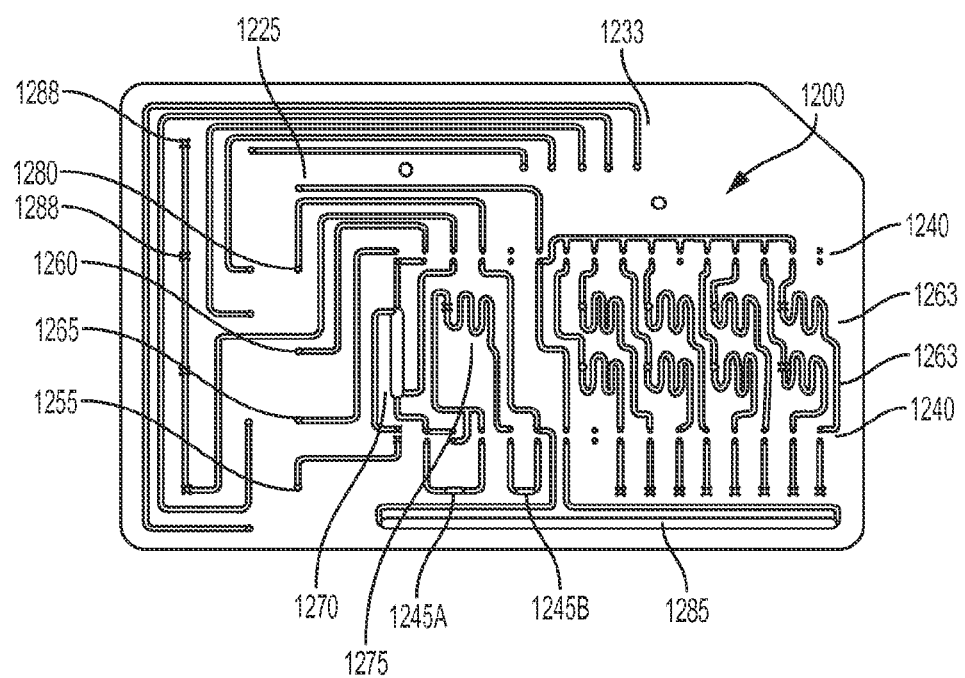
FIG. 12 illustrates an integrated biochip configured to be connected to an integrated cartridge according to an embodiment of the invention.

FIG. 12 illustrates the integrated biochip without the cartridge. The biochip 1200 uses a parallel detection approach, similar to the biochip 500, and includes 8 detection chambers 1263. In some embodiments, the separation and detection chambers are optionally made to be wide meander channels rather than a circular chamber. Typically, if a circular chamber is several times larger than the size of an incoming channel (e.g. >2 or 3 times), then fluid will break apart when it flows from the small channel to the large circular chamber. To reduce the improper filling of fluid, we introduce "a transition channel" as described above. Using the transition channel, the size of the incoming channel gradually increases to finally lead into the circular chamber. This method avoids fluid breaking and bubbles in the chamber when the fluid flows at a slow rate. However, when the fluid moves at a higher flow-rate, the fluid can occasionally break-up and create air bubbles in the circular chamber even with the transition channel. Thus, the circular chamber may not be completely filled with the fluid. In contrast, a wide meander channels can be more effective for smaller volumes (e.g. less than 20 uL).

In some embodiments, the meander channels (i.e. the separation and detection chambers) are designed within a circular periphery. This design enables a detection instrument to read the fluorescence signal for either the 'meander design' or 'circular chamber design'. Thus, in some embodiments the wide meander channel is replaced with a circular chamber.

Similar to the biochip 700, in some embodiments the biochip 1200 includes a sample preparation chamber 1270, an elution vent chamber 1245A, an amplification vent chamber 1245B, an amplification chamber 1275, a post-amplification vent chamber 1285, and flow gates 1240. The biochip 1200 also optionally includes pneumatic/air lines 1233. Other embodiments of the biochip includes some, but not all, of the components listed above.

The elution vent chamber 1245A allows the air in the elution buffer chamber to be vented outside of the biochip, and the amplification vent chamber 1245B allows the air in the amplification chamber to be vented outside of the biochip.

In some embodiments, the pneumatic/air lines 1233 provides connection to the biochip assembly. As shown in FIG. 12, the system interfaces all of the flow-connectors with pneumatic air-lines. Then, the system can use the same interface to deliver air to the cartridge, rather than a separate mechanism on top of the cartridge to supply air as described above. In some embodiments, the pneumatic air lines deliver the air from the biochip to the bottom of the cartridge. Then, the air is routed through a vertical channel from the bottom to the top of the cartridge and is delivered to the top of the fluid reservoirs. Each fluid reservoir has a dedicated pneumatic air line from the biochip to the top of the fluid reservoir in the cartridge.

The biochip 1200 includes various fluid input ports, including waste liquid output ports 1288, a sample and lysis buffer input port 1255, an elution buffer input port 1265, a sample preparation wash buffer input port 1260, a post-amplification buffer input port 1280, and a separation wash buffer input port 1225.

In some embodiments, a pre-filled buffer cartridge is incorporated as part of an assembled biochip. The buffers in the cartridge can be driven pneumatically when the biochip is placed on the instrument and interface with the pneumatic manifold in the instrument. The cartridge also has optional empty chambers to serve as waste chambers for unloading buffers after each bioassay process in the biochip. This cartridge assembly can enable fully automated operation and eliminate the need for the operator to use syringes and their connection to the biochip. The assembly of the cartridge and biochip is illustrated below in connection with the descriptions of FIGS. 15-17.

Figure 13:
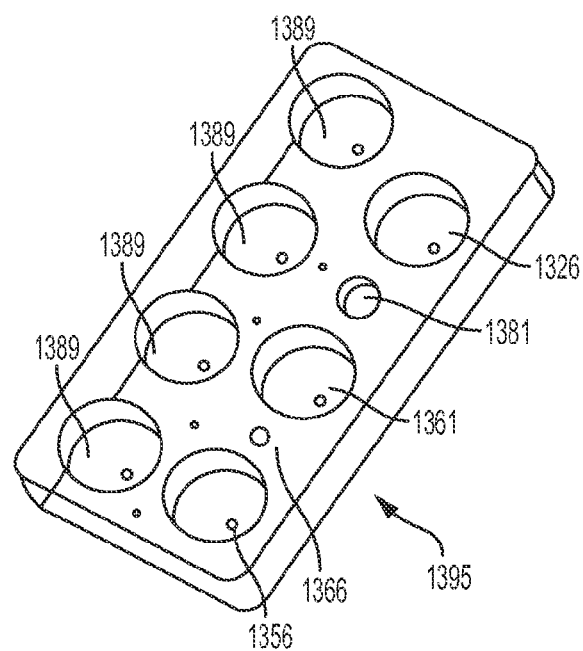
FIG. 13 illustrates an integrated cartridge configured to be connected to an integrated biochip according to an embodiment of the invention.

FIG. 13 illustrates the integrated cartridge 1195 separate from the integrated biochip 1200. The integrated cartridge 1195 contains a number of reservoirs connected to input ports on the integrated biochip 1200. Exemplary reservoirs are waste reservoirs 1389 (connected to the waste liquid output ports 1288), sample and lysis buffer reservoir 1356 (connected to the sample and lysis buffer input port 1255), an elution buffer reservoir 1366 (connected to the elution buffer input port 1265), a sample preparation wash buffer reservoir 1361 (connected to the sample preparation wash buffer input port 1260), a post-amplification buffer reservoir 1381 (connected to the post-amplification buffer input port 1280), and a separation wash buffer reservoir 1326 (connected to the separation wash buffer input port 1225). In some embodiments, the reservoirs is pre-filled with reagents. The waste liquid output reservoirs 1389 are initially empty, but is filled up with the waste from the separation and detection chambers. There can be multiple waste liquid output reservoirs, or one large reservoir. In some embodiments, the reservoirs have the same size, but the size can be different for different reservoirs.

Some embodiments of the buffer cartridge 1495 have a rubber material between the top cover and the cartridge body. In some embodiments, there exists an opening on the top cover for the sample introduction (for example from a syringe, pipette, or even to introduce a swab top into the cartridge). The rubber directly below this opening has a sealable opening. In some embodiments, the sealable opening is a slit. When a pipette, syringe, or swab, is thrust into the rubber slit, the rubber opens to provide access to the reservoir in the buffer cartridge to enable the user to deposit the sample inside the cartridge. When the pipette/syringe is retracted, the elasticity of the rubber ensures that it closes the slit, shutting-off access to the reservoir. This air tight self-seal created by the rubber ensures that any environmental contaminant is not subsequently introduced into the reservoir and the self-seal also prevents or minimizes pneumatic/air leak from the reservoir when the buffer/sample is driven pneumatically from this reservoir in the cartridge into the biochip.

FIGS. 14A and 14B illustrates embodiments of a buffer cartridge 1495 with a self-sealing rubber gasket. In some embodiments, the cartridge 1495 includes sample reservoirs 1490 and a rubber material 1492 on top of the reservoirs. On top of the rubber material 1492, there is a top cover 1493, which can be plastic. In some embodiments, the top plastic, rubber, cartridge and biochip are affixed/bonded to constitute a fully assembled biochip with the integrated buffer cartridge 1495. The top cover has a hole 1462, to which a pipette 1467, syringe or swab can be introduced. Immediately below the hole 1462, there is a rubber slit 1468 that can be open to provide access to sample reservoirs 1490. In some embodiments, the slit is a straight line, a 'X' pattern, or a 'star' pattern.

In some embodiments, the thickness of the rubber material 1492 ranges from 0.5 mm to 50 mm. The material is, for example, silicone, PTFE, neoprene, polyethelene, polymide, polycarbonate, acrylic, cyclo-olyfin polymers, cyclo olefin polymers, or any other material that has elasticity similar to that of rubber or elastomer. The durometer for example is Shore A 50 durometer, as used in one demonstration. The slit 1468 in the rubber that provides access to the sample reservoir below is, for example, between 0.5 mm and 25 mm, or larger as required. Thicker rubber and/or harder material durometer will require higher mechanical force by the operator to open the slit in the rubber to access the sample reservoir in the cartridge. Nevertheless, thicker rubber and/or harder material durometer can be advantageous as they can provide better self-sealing and can prevent or reduce air leak when pneumatic pressure is applied inside the sample reservoir in the cartridge to drive the sample into the biochip.

In another exemplary configuration, the hole 1462 has a diameter of ~4 mm, and the top cover 1493 is ~2 mm thick. Also, the slit size is ~2.5 mm, and the top cover is an acrylic cover. The rubber material 1492 beneath the top cover 1493 is ~3 mm thick and Shore A, 50 durometer.

Figure 15A:
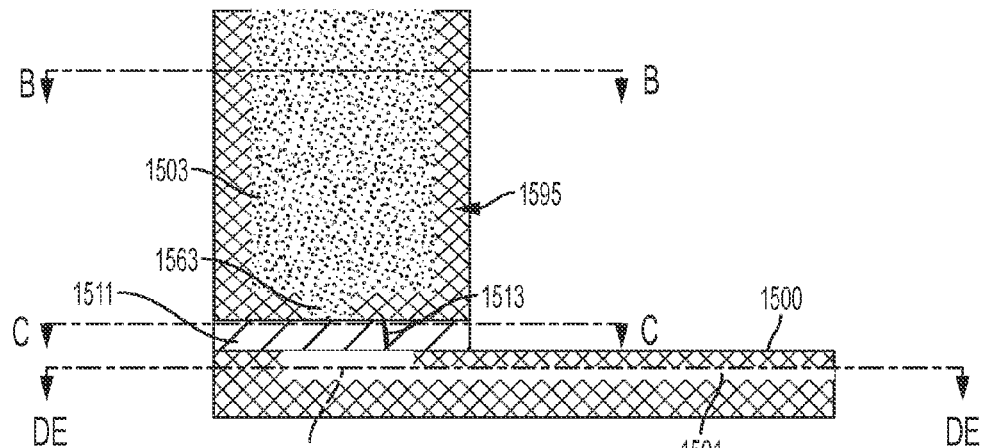
FIG. 15A illustrates a cross-sectional side view of a cartridge, membrane and biochip stack according to an embodiment of the invention.

FIG. 15A illustrates a cartridge, membrane and biochip stack bonded together according to some embodiments. In some embodiments, the biochip, membrane, and cartridge are manufactured separately as independent modules and then be mated and joined/bonded. In alternative embodiments, the biochip and cartridge are fabricated as a single unit. The stack can be bonded by adhesive or clamped by various mechanisms. The cartridge 1595 has a hole 1563 to allow fluid to flow out of the cartridge to the biochip 1500. The membrane 1511 has a slit 1513 that controls the flow of fluid 1503 from the cartridge 1595 to the biochip 1500. In some embodiments, the slit 1513 is located anywhere above the chamber 1517 of the biochip. To provide area for the slit 1513 to open, the chamber 1517 is optionally made larger than input ports of biochip 700. In FIG. 15, by placing the slit 1513 offset from the hole 1563 (i.e., not directly under the hole), leakage through the slit is prevented or minimized when the slit is not open and/or there is backpressure from the fluid/air from the biochip to the reservoir. If the slit was located directly under the hole, there is no object blocking the slit from opening upward when there is backpressure (i.e. fluid trying to enter from the biochip into the cartridge-reservoir). The membrane will stretch upwards into the hole and eventually open as the fluid pressure from the biochip increases allowing fluid flow in the reverse direction. However, if the slit 1513 is offset from the hole 1563, the slit cannot open because it will be thrust against the body of the cartridge.

Other properties of the membrane and the biochip are described below. Some of the exemplary materials of the membrane are silicone, latex, PTFE, and polyethylene. In some embodiments, thickness ranges from 0.001" to 0.1". The thicker the material, the more pressure required to open the slit 1513 and to enable fluid flow across membrane through the slit. Some embodiments of the chamber 1517 are larger than the size of the hole 1563 of the cartridge. The chamber is connected to a channel 1501 through which the fluid will flow to reach its destination.

Figure 15B:
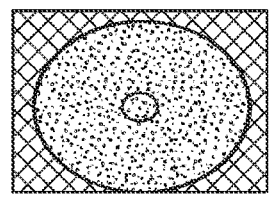
FIG. 15B illustrates a cross-sectional view (B-B) of the cartridge of FIG. 15A according to an embodiment of the invention.
Figure 15C:
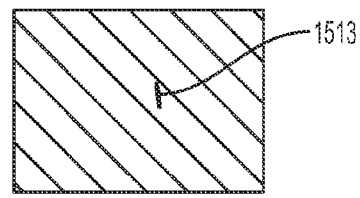
FIG. 15C illustrates a cross-sectional view (C-C) of the membrane of FIG. 15A according to an embodiment of the invention.
Figure 15D:
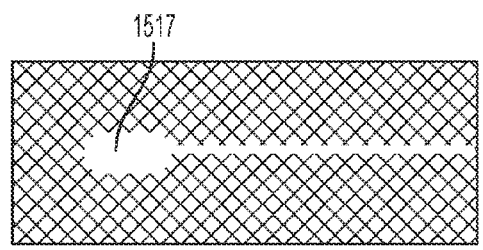
FIG. 15D illustrates a cross-sectional view (DE-DE) of the biochip of FIG. 15A according to an embodiment of the invention.
Figure 15E:
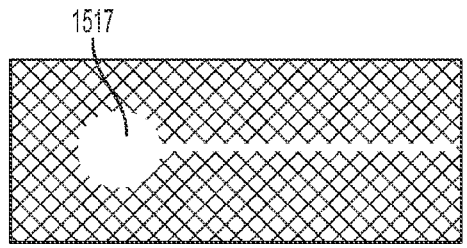
FIG. 15E illustrates a cross-sectional view (DE-DE) of the biochip of FIG. 15A according to an embodiment of the invention.

FIG. 15B is a B-B cross-sectional view of the cartridge 1595. FIG. 15C is a C-C cross-sectional view of the membrane 1511 with the slit 1513. FIGS. 15D and 15E are DE-DE cross-sectional views of the biochip 1500. Different embodiments of the chamber 1517 of the biochip have different shapes (e.g., slot, circular, oval).

Figure 16A:
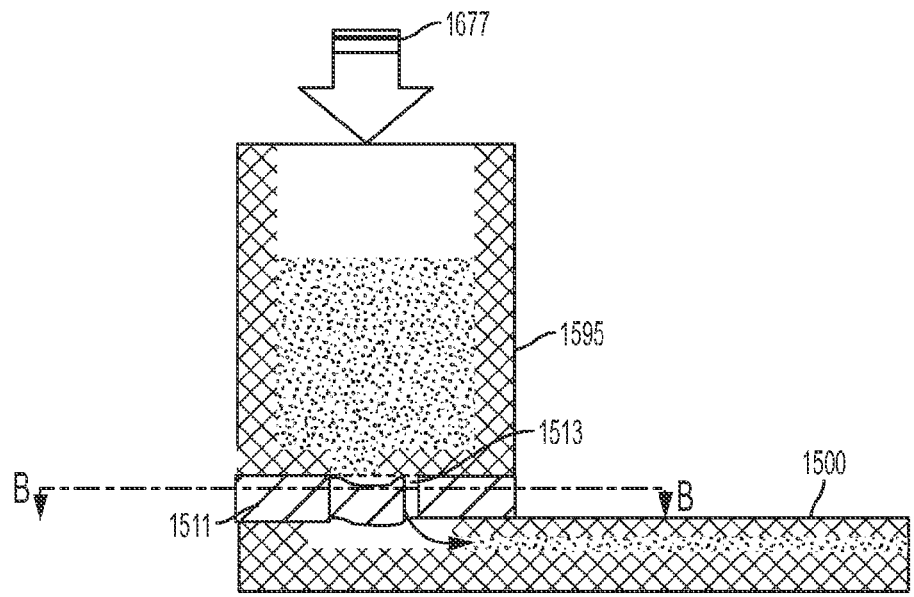
FIG. 16A illustrates a cross-sectional side view of the stack of FIG. 15A with an open membrane slit according to an embodiment of the invention.
Figure 16B:
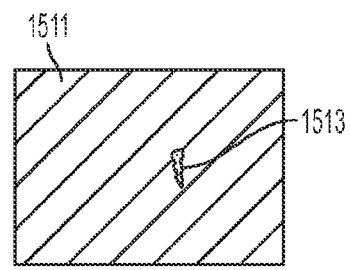
FIG. 16B illustrates a cross-sectional view (B-B) of the membrane of FIG. 16A with an open slit according to an embodiment of the invention.

FIG. 16A illustrates a cross-sectional side view of the stack of FIG. 15A with an open membrane slit according to an embodiment of the invention. When pneumatic/air pressure 1677 is applied from the top of the cartridge 1595, the pressure will be applied downward to the slit 1513 and open the slit. Then the fluid flows from the cartridge 1595 to the biochip 1500. FIG. 16B is a B-B cross-sectional view of the membrane 1511 with the open slit 1513.

Figure 17A:
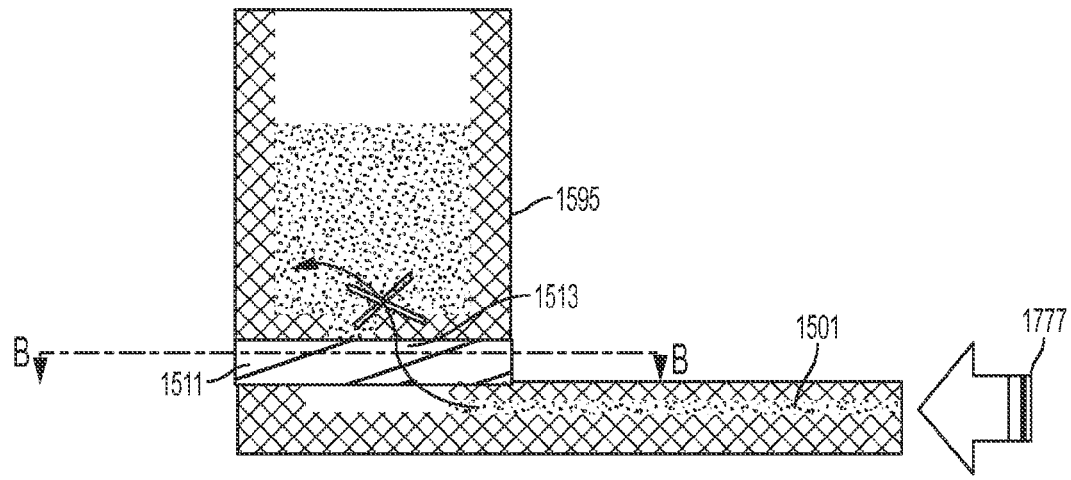
FIG. 17A illustrates a cross-sectional side view of the stack of FIG. 15A with a closed membrane slit according to an embodiment of the invention.
Figure 17B:
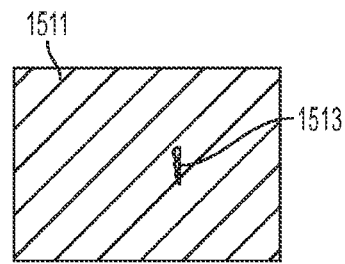
FIG. 17B illustrates a cross-sectional view (B-B) of the membrane of FIG. 17A with a closed slit according to an embodiment of the invention.

FIG. 17A illustrates a cross-sectional side view of the stack of FIG. 15A with a closed membrane slit according to an embodiment of the invention. Unlike the downward pressure 1677 of the FIG. 16A, the pressure 1777 from the other side of the channel will create upward pressure on the membrane 1511. As illustrated above, because the bottom portion of the cartridge 1595 is placed against the membrane 1511, the bottom portion of the cartridge prevents the slit 1513 from opening upward. As a result of the closed slit, fluid cannot flow from biochip to the cartridge. FIG. 17B is a B-B cross-sectional view of the membrane 1511 with the closed slit 1513.

In the examples provided above, only one type of DNA probe was included in each of the separation and detection chambers and one type of fluorescent label was used. However, because the separation and detection chambers physically separate the different DNA fragments via binding to the DNA probes, multiple types of DNA probes and multiple types of fluorescent dyes can be used in other implementations. For example, a biochip that is able to separate and detect 30 different types of DNA fragments in six different separation and detection chambers is within the scope of the invention. In such an embodiment, a collection of 30 different types of amplification primers (either by PCR or other amplification methods) are supplied that include only five different fluorescent labels, each label having a different emission color. Thus, after amplification (assuming each DNA target fragment is present in the sample), the post-amplification solution will contain a collection of 30 different types of DNA fragments, but these fragments will only be labeled with five distinct colors. Using known methods, one would not be able to distinguish the DNA fragments that are labeled with the same color from each other.

In embodiments of the present invention, five different DNA probes can be immobilized in each of the six separation and detection chambers, for a total of 30 different types of DNA probes in the biochip as a whole. Each of the five different types of DNA probes in a particular chamber will correspond to a different label color. In this way, the biochip captures five different DNA fragment types per chamber, each being labeled with a different color fluorescent label. Thus, because each chamber now only has one type of DNA fragment per color in each chamber, the interference between the labels emitting the same color is reduced or eliminated.

Implementations of the invention enable a gas to be introduced into one or more of the separation and detection chambers after the target DNA fragments have been bound to the DNA probes immobilized therein. This enables the removal of substantial amounts of any buffers or other non-bound material from the separation and detection chamber, thereby enabling the fluorescence to be detected on a dry basis.

One having ordinary skill in the art will recognize that the embodiments set forth herein are merely illustrative of the present invention. Thus, the techniques, devices, and system described above can be modified to enable known genetic material amplification methods to be performed while remaining within the scope of the invention.

Testing Platform

Figure 18:
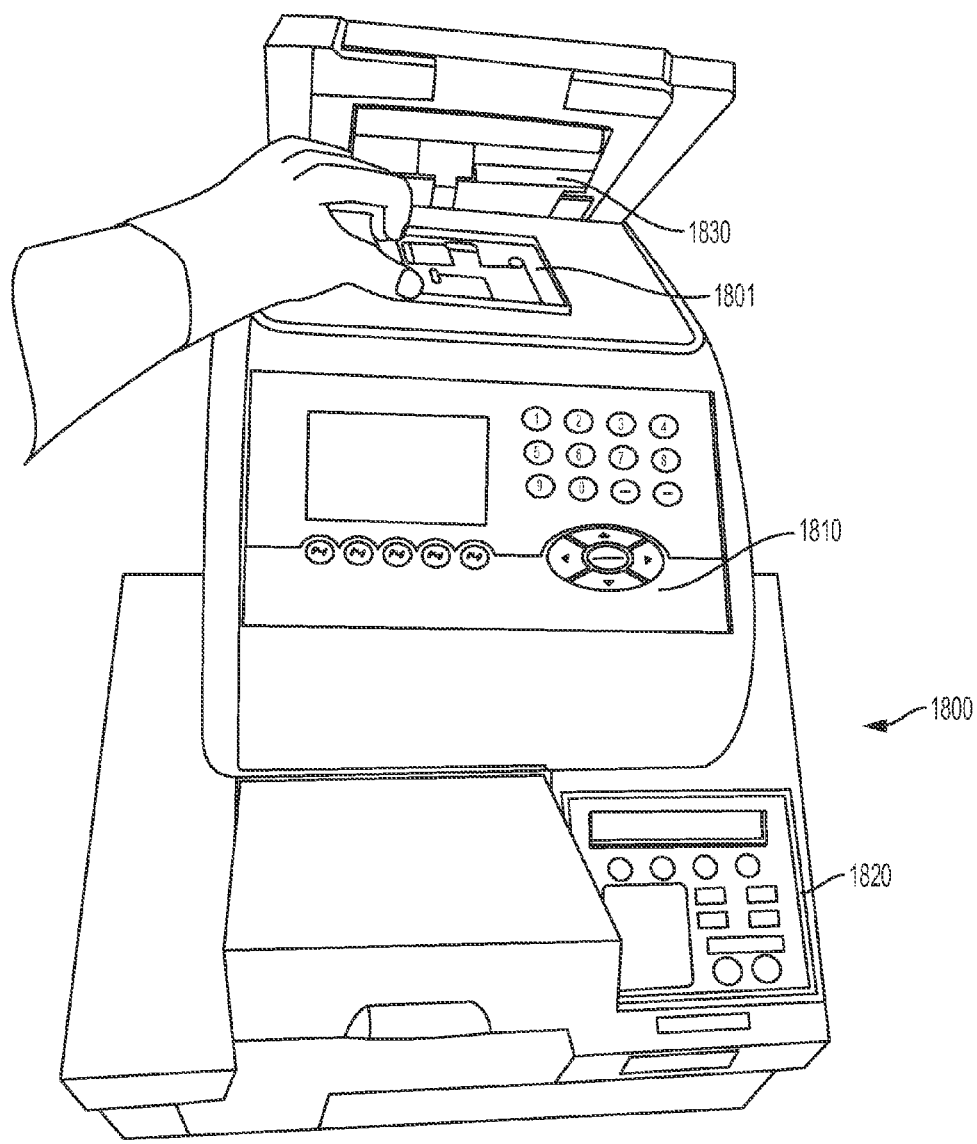
FIG. 18 illustrates a testing platform according to an embodiment of the invention.

FIG. 18 depicts a genetic testing platform 1800 including a compact processor unit 1810 and a table-top reader unit 1820 according to embodiments of the present invention. In some embodiments, the units draw power from a standard 110V/220V wall outlet. The processor unit includes a bottom rapid peltier based thermocycler module to provide heat required for cell lysis, DNA elution, reverse-transcriptase and amplification. The processor also includes a top programmable pneumatic (0-100 psig) module 1830 for fluid flow control in the integrated biochip 1801. In alternative embodiments, there are two or more separate units for providing heat, providing pressure, and reading fluorescence.

In some embodiments, the reader unit is FDA classified for in-vitro diagnostic use. The 2-unit instrument platform offers significant capital cost savings for customers who desire to simultaneously run several samples on individual biochips (e.g., on-demand, Random Access Testing). For example, customers can easily set up a bench-top work station with a number of processor units (e.g. 2 to 50) and only one reader unit. Multiple samples can be simultaneously prepared on the biochip in less than 5 minutes per sample, tested in individual processor units in about 90 minutes, and sequentially read by the reader unit in less than 2 minutes per chip.

In some embodiments, to perform a diagnostic test, the integrated biochip is placed in the processor unit between the top pneumatic module and bottom peltier module. This standalone setup enables the integrated biochip to perform diagnostic test processes such as cell lysis, nucleic acid extraction, nucleic acid capture, nucleic acid purification, reagent mixing, reverse-transcriptase reaction and amplification, sequentially executed in an integrated manner in the disposable biochip. Typical processing time from providing sample to complete multiplex amplification is under 90 minutes. Upon completion, the integrated biochip is transferred to the tabletop reader unit for a fluorescence read of amplified DNA fragments, which is typically accomplished in under 2 minutes. The reader unit has a multi-color excitation-emission optical filter system and utilizes highly sensitive photomultipler tube detection. This reader demonstrated to accurately detect fluorescent signal from even a single copy of amplified DNA.

Experimental Data

This section provides test data for the biochip and method described above. Ultramer/DNA of 4 respiratory pathogens (purchased from IDT Technologies, CA), namely, Influenza-A, Influenza-B, Influenza-A/H1 and Influenza-A/H3, at 100000 copies each were spiked into 10 µL of human blood sample. FIG. 19A lists the forward primer, reverse primer, probe sequences of the four respiratory pathogens mentioned above. FIG. 19B lists two common quencher sequences that are used in this experiment. The sample was then used for processing on biochip.

A common quencher oligonucleotide is a random DNA sequence of 8-20 bp lengths. A common quencher oligonucleotide with a dye-quencher moiety can be used for quenching the fluorescence of the probe. For example, in the first sequence of FIG. 19B, the random DNA sequence is 5'-TGTTATTCAGT (SEQ ID NO: 14) and the dye-quencher moiety is 3IAbRQSp. The probe includes a gene specific sequence to bind with a target DNA and a common quencher complementary sequence (e.g., complementary sequence to TGTTATTCAGT (SEQ ID NO: 1)) to bind with a common quencher. The common quencher complementary sequence of the probe contains fluorescence, and when a common quencher oligonucleotide binds to the probe, the fluorescence of the probe will be quenched. This configuration of probe allows binding of a common quencher oligonucleotide to the probe containing a complementary quencher sequence. Thus, one or few common quencher oligonucleotides can be used for a plurality of probes designed to bind to their corresponding DNA targets. The detailed description of the probe and the common quencher oligonucleotide can be found in the incorporated application, entitled "Method for Separation and Detection of DNA Fragments."

The sample prep-process utilized the reagents from a commercially available kit, easyMAG™ (bioMérieux, Inc, NC) which includes the lysis buffer, magnetic beads for nucleic acid capture, wash buffer and elution buffer. Briefly, the spiked sample was input into 100 µL, of lysis buffer containing magnetic beads to capture nucleic acid. The solution was incubated for about 5 min.

After incubation, pneumatic pressure provides the flow of such solution through the sample preparation chamber capturing the magnetic beads inside the chamber since a magnet was positioned above (and outside) the sample-prep chamber. The retained magnetic beads would have nucleic acid bound to it from earlier the lysis incubation chemistry. Next, wash buffer 1000 µL, that flowed through the magnetic beads washed the beads and removed components of the lysis buffer (for example, Chaotropic salts) and other biological elements (e.g. extracellular compounds, proteins). Subsequently, the introduction of the elution buffer 20 µL to the magnetic beads and incubation for about 3 min released the nucleic acid from the magnetic beads into the elution buffer. Next, pneumatic pressure moved the elution buffer containing the nucleic acid/ DNA into the PCR/isothermal amplification chamber. The elution buffer was mixed with Qiagen multiplex PCR Kit (cat #206152, Qiagen, CA), HotStar polymerase (1 U per reaction) and forward and reverse primers for each of the 4 DNA targets at concentration of 0.2 µM each. The designed primers for the 4 targets are listed in FIG. 19 below. Multiplex PCR was then performed in which all for targets are amplified in the same reaction. PCR thermal cycling conditions were, 96° C. for 10 min for initial denaturation followed by 40 cycles of 96° C. for 1 min, 60° C. for 1 min, 72° C. for 1 min, and final extension at 72° C. for 5 min.

Upon completion of PCR amplification, the PCR amplicons moved to the post-amplification vent chamber where it was mixed with about ~70 µL of the post-amplification buffer, in this case deionized water, to a volume of ~90 µL including the PCR amplicons from the PCR chamber. Next, pneumatic pressure applied to the input channels moved the solution from the 'post-amplification vent chamber' into 4 detection chambers. Each of the four detection chambers contained probe and quencher for only one targets, all labeled with FAM dye. When the 90 µL of reconstituted PCR amplicons flowed into the four detection chambers, it was mixed with the probe and quencher present in its respective chambers. Chamber 1 contained the probe and quencher for Influenza-A, chamber 2 for Influenza-B, chamber 3 for Influenza-A/H1 and chamber 4 Influenza-A/H3. The probe and common quencher sequence for these targets is also listed in FIG. 19. The probe and the common-quencher oligo containing BHQ quencher were at equimolar concentration of 0.2 µM contained in ~5 µL solution and all probes were labeled with Cy5 dye. With ~25 µL capacity in each detection chamber, approximately 20 µL of the reconstituted PCR amplicon was filled into each chamber simultaneously. Closing the flow gates leading into an unused detection chamber restricted the flow into unused detection chambers.

Once the PCR amplicon was loaded into all 4 detection chambers simultaneously, the temperature was ramped from ~25° C. (room temperature) to 94° C. at the rate of 1.5° C.-2.5° C. per second. After the temperature reached 94° C., from the temperature was ramped down from 94° C. to 25° C. at a ramp down rate of 2° C.-4° C. per second. This ramp up and ramp down allowed for the different denaturing and annealing interactions between the PCR amplified amplicons, probes and primers, as described in the incorporated application: "Method for Separation and Detection of DNA Fragments." Finally, a fluorescence reader (FLX800T, BioTek Instruments, VT) as shown below measures the fluorescence of Cy5 in each of the 4 chambers. Presence of Cy5 fluorescence in each chamber indicated the successful binding of a PCR amplicon to the corresponding detection probe present in that chamber. FIG. 20 shows the increases in probe fluorescence [in relative fluorescence units (RFU)] for each of the 4 targets (Influenza-A, Influenza-B, Influenza-A/H1, Influenza-A/H3). Using this detection method of the present invention and using only single color fluorescence, we demonstrated the detection of 4 targets in this example.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

The invention claimed is:

1. A flow gate, comprising:
   a first port and a second port separated by a junction, each port being a small chamber at an end of a channel; and
   a thin flexible material adhered across the first and second ports and disposed over the junction,
   wherein the flow gate is capable of being in an open configuration and a closed configuration, wherein the thin flexible material is configured so that pressure applied to the thin flexible material changes the flow gate between the open configuration and the closed configuration, the open configuration having space between the thin flexible membrane and the junction and permitting fluid flow between the two channels through the ports, and the closed configuration having the thin flexible membrane in contact with the junction and inhibiting fluid flow between the two channels.

2. The flow gate of claim 1, wherein the thin flexible material is plastic.

3. The flow gate of claim 1, wherein the pressure applied to the thin flexible material is pneumatic pressure.

4. The flow gate of claim 1, further comprising at least one layer of material disposed above the ports.

5. The flow gate of claim 4, wherein the flow gate is in the open configuration without the application of the pressure and wherein the application of the pressure changes the flow gate from the open configuration to the closed configuration.

6. The flow gate of claim 4, wherein the flow gate is in the closed configuration without the application of the pressure and wherein the application of the pressure changes the flow gate from the closed configuration to the open configuration.

7. The flow gate of claim 1, wherein the thin flexible material is adhered to at least a portion of the junction separating the first and second ports to inhibit fluid flow between the two channels, wherein the adhesion is configured to be delaminated by fluid pressure in at least one of the channels above a threshold pressure.

8. The flow gate of claim 7, wherein an adhesive adhering the thin flexible material to the portion of the junction is configured to remain delaminated after delamination by the fluid pressure.

* * * * *